United States Patent
Miyake et al.

(10) Patent No.: US 10,252,995 B2
(45) Date of Patent: Apr. 9, 2019

(54) METHOD FOR PRODUCING 1-(4-HYDROXYPHENYL)-4-(4-TRI-FLUOROMETHOXYPHENOXY)PIPERIDINE OR SALT THEREOF

(71) Applicant: OTSUKA PHARMACEUTICAL CO., LTD., Tokyo (JP)

(72) Inventors: Masahiro Miyake, Osaka (JP); Aya Asahina, Osaka (JP); Takahiro Okada, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 0 days.

(21) Appl. No.: 15/561,602

(22) PCT Filed: Mar. 25, 2016

(86) PCT No.: PCT/JP2016/059599
§ 371 (c)(1),
(2) Date: Sep. 26, 2017

(87) PCT Pub. No.: WO2016/158737
PCT Pub. Date: Oct. 6, 2016

(65) Prior Publication Data
US 2018/0065931 A1  Mar. 8, 2018

(30) Foreign Application Priority Data
Mar. 27, 2015 (JP) ................. 2015-065824
Feb. 26, 2016 (JP) ................. 2016-036290

(51) Int. Cl.
C07D 211/46 (2006.01)
C07B 37/04 (2006.01)
A61K 31/4465 (2006.01)
A61K 31/424 (2006.01)

(52) U.S. Cl.
CPC .......... *C07D 211/46* (2013.01); *A61K 31/424* (2013.01); *A61K 31/4465* (2013.01); *C07B 37/04* (2013.01)

(58) Field of Classification Search
CPC ............... C07D 211/46; A61K 31/424; A61K 31/4465; C07B 37/04
USPC ....................................................... 546/216
See application file for complete search history.

(56) References Cited

U.S. PATENT DOCUMENTS 4,024,196 A * 5/1977 Krekeler ................. C07C 37/07
568/772
4,410,708 A 10/1983 Yahagi et al.
2006/0094767 A1 5/2006 Tsubouchi et al.

FOREIGN PATENT DOCUMENTS

| JP | 56-073048 A | 6/1981 |
|---|---|---|
| JP | 58-118545 A | 7/1983 |
| JP | 05-085994 A | 4/1993 |
| JP | 2003-096030 A | 4/2003 |
| JP | 2004-149527 A | 5/2004 |
| JP | 2005-330266 A | 12/2005 |
| JP | 2009-534291 A | 9/2009 |
| WO | 2005/092832 A1 | 10/2005 |
| WO | 2008/140090 A1 | 11/2008 |
| WO | WO 2011/093529 A1 * | 8/2011 |

OTHER PUBLICATIONS

Hirofami Sasaki, et al., "Synthesis and Antituberculosis Activity of a Novel Series of Optically Active 6-Nitro-2,3-dihydroimidazo[2,1-b]oxazoles", Journal of Medicinal Chemistry, vol. 49, No. 26, 2006, pp. 7854-7860.
Marius H. Terdic, et al., "Disubstituted phenothiazones. III. Syntheses of dimethyl-3H-phenothiazin-3-ones", Bevue Roumaine de Chimie, vol. 30, No. 2, 1985, pp. 133-139.
Marius H. Terdic, et al., "Disubstituted phenothiazones. II. New halogeno-3H-phenothiazin-3-ones", Bevue Roumaine de Chimie, vol. 29, No. 6, 1984, pp. 489-495.
International Search Report for PCT/JP2016/059599 dated Jun. 28, 2016 [PCT/ISA/210].
Partial Supplementary European Search Report dated Jul. 31, 2018, issued by the European Patent Office in corresponding EP Application No. 16772618.1.

* cited by examiner

*Primary Examiner* — Daniel R Carcanague
(74) *Attorney, Agent, or Firm* — Sughrue Mion, PLLC

(57) ABSTRACT

The present invention provides a method for producing 1-(4-hydroxyphenyl)-4-(4-trifluoromethoxyphenoxy)piperidine or a salt thereof, the method including the step of heating hydroquinone and 4-(4-trifluoromethoxyphenoxy)piperidine. This method can produce 1-(4-hydroxyphenyl)-4-(4-trifluoromethoxyphenoxy)piperidine or a salt thereof in an industrially advantageous manner.

11 Claims, No Drawings

METHOD FOR PRODUCING 1-(4-HYDROXYPHENYL)-4-(4-TRIFLUOROMETHOXYPHENOXY)PIPERIDINE OR SALT THEREOF

CROSS REFERENCE TO RELATED APPLICATIONS

This application is a National Stage of International Application No. PCT/JP2016/059599, filed on Mar. 25, 2016, which claims priority from Japanese Patent Application No. 2015-065824, filed on Mar. 27, 2015 and Japanese Patent Application No. 2016-036290, filed on Feb. 26, 2016, the contents of all of which are incorporated herein by reference in their entirety.

TECHNICAL FIELD

The present invention relates to a method for producing 1-(4-hydroxyphenyl)-4-(4-trifluoromethoxyphenoxy)piperidine or a salt thereof, and use thereof.

BACKGROUND ART 1-(4-Hydroxyphenyl)-4-(4-trifluoromethoxyphenoxy)piperidine and salts thereof are compounds that are useful as an intermediate in the synthesis of various pharmaceutical compositions (preferably antitubercular agents), agricultural chemicals, etc.

A method comprising reacting a cyclohexanedione compound and an amine compound under neutral or basic conditions is known as a method for producing 1-(4-hydroxyphenyl)-4-(4-trifluoromethoxyphenoxy)piperidine (Patent Literature (PTL) 1).

Since this method requires oxidizing an intermediate with oxygen to obtain the desired product, an operation of passing air or oxygen through the reaction system is essential. However, the operation of passing air or oxygen through the reaction system requires a special device, as well as complicated steps of supplying an appropriate amount of oxygen in accordance with the progress of the reaction. When oxygen is not present in the reaction system, the reaction progresses only up to the formation of an imine, and thus fails to efficiently obtain the desired product.

Further, to supply oxygen to the reaction system, oxygen must be dissolved in a solvent. Therefore, a certain amount of solvent is necessary for the reaction. Further, to supplement the solvent that decreases mainly due to evaporation by aeration, appropriately adding the solvent is also required. Accordingly, the amount of organic solvent used inevitably becomes large, which is environmentally unfriendly. Furthermore, when this reaction is carried out on a large scale, performing the reaction with good repeatability is difficult. In addition, since the reaction requires heating in the presence of an organic solvent and oxygen for a long time, anti-combustion measures must also be taken.

Further, since the cyclohexanedione compound, used as a reactant, is a compound obtained from the corresponding aromatic compound by adding high-pressure hydrogen, the method disclosed in PTL 1 is not preferable in terms of supplied amount and cost. The desired aminophenol compound, which has an electron-rich aromatic ring, is extremely unstable to oxidizing conditions. Therefore, even if the conditions are highly optimized, the oxidation reaction progresses excessively under oxygen oxidation conditions, and purification of by-products is inevitable, thus requiring a great deal of labor for complicated purification of byproducts, management for preventing oxidation byproducts, etc.

Thus, the method disclosed in PTL 1 has unsolved problems in terms of costs, supplied amount, etc., and is not an industrially preferable method.

As methods for introducing an amino group into an aromatic compound, reaction systems using a metal catalyst or the like are also known. However, such a method is not industrially preferable, because using a metal catalyst increases the number of steps and costs. All such known methods have high production costs, and a more inexpensive production method has been desired for pharmaceutical compositions assumed to be supplied to developing countries, such as antitubercular agents.

Patent Literature (PTL) 2 discloses a method for producing a specific N,N-dialkylaminophenol by reacting a dihydric phenol with a specific secondary amine. However, this method does not produce 1-(4-hydroxyphenyl)-4-(4-trifluoromethoxyphenoxy)piperidine. Furthermore, in order to prevent the reduction of reaction efficiency due to increased basicity of the reaction system, this method requires using a secondary amine in an amount that is more than the amount of dihydric phenol.

CITATION LIST

Patent Literature

PTL 1: WO2005/092832
PTL 2: JPH05-85994A

SUMMARY OF THE INVENTION

Technical Problem

The present invention provides a method for producing 1-(4-hydroxyphenyl)-4-(4-trifluoromethoxyphenoxy)piperidine or a salt thereof in an industrially advantageous manner.

Solution to Problem

The present inventors conducted extensive research to solve the above problem. As a result, the present inventors found that the above problem can be solved by heating a mixture of hydroquinone and 4-(4-trifluoromethoxyphenoxy)piperidine. The present invention has been accomplished based on this finding.

The present invention, for example, includes the following production methods described in Items 1 to 11.

Item 1. A method for producing 1-(4-hydroxyphenyl)-4-(4-trifluoromethoxyphenoxy)piperidine represented by Formula (1):

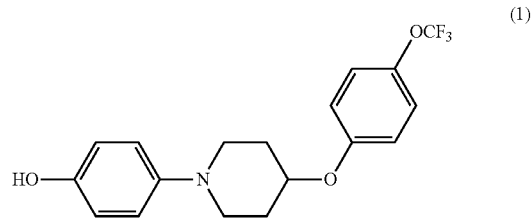 [SMILES: Oc1ccc(N2CCC(Oc3ccc(OC(F)(F)F)cc3)CC2)cc1]

or a salt thereof, the method comprising the step of heating hydroquinone represented by Formula (2):

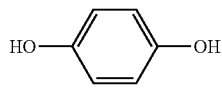

or a salt thereof and
4-(4-trifluoromethoxyphenoxy)piperidine represented by Formula (3):

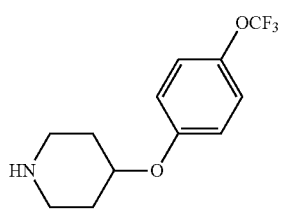

or a salt thereof,
the hydroquinone represented by Formula (2) being used in an amount of 1.5 moles or more per mole of the 4-(4-trifluoromethoxyphenoxy)piperidine represented by Formula (3).

Item 2. The production method according to Item 1, wherein the hydroquinone represented by Formula (2) or a salt thereof is used in an amount of 2 to 10 moles per mole of the 4-(4-trifluoromethoxyphenoxy)piperidine represented by Formula (3) or a salt thereof.

Item 3. The production method according to Item 1 or 2, wherein the heating step comprises heating at 150° C. or more (preferably 150 to 300° C.)

Item 4. The production method according to any one of Items 1 to 3, wherein the heating step is performed under solvent-free conditions.

Item 5. The production method according to any one of Items 1 to 4, wherein the heating step is performed under an inert atmosphere.

Item 6. The production method according to any one of Items 1 to 5, further comprising the step of forming the 1-(4-hydroxyphenyl)-4-(4-trifluoromethoxyphenoxy)piperidine into a salt by using an acid compound.

Item 7. A method for producing the compound represented by Formula (12)

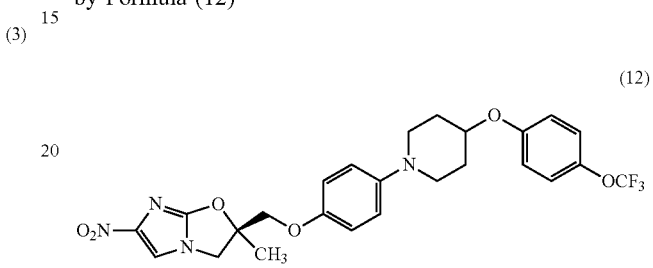

or a salt thereof,
the method comprising the steps of:
(a) producing 1-(4-hydroxyphenyl)-4-(4-trifluoromethoxyphenoxy)piperidine or a salt thereof by the method according to any one of Items 1 to 6; and
(b) producing the compound represented by Formula (12) or a salt thereof by using 1-(4-hydroxyphenyl)-4-(4-trifluoromethoxyphenoxy)piperidine or a salt thereof as a starting material.

Item 8. The method according to item 7,

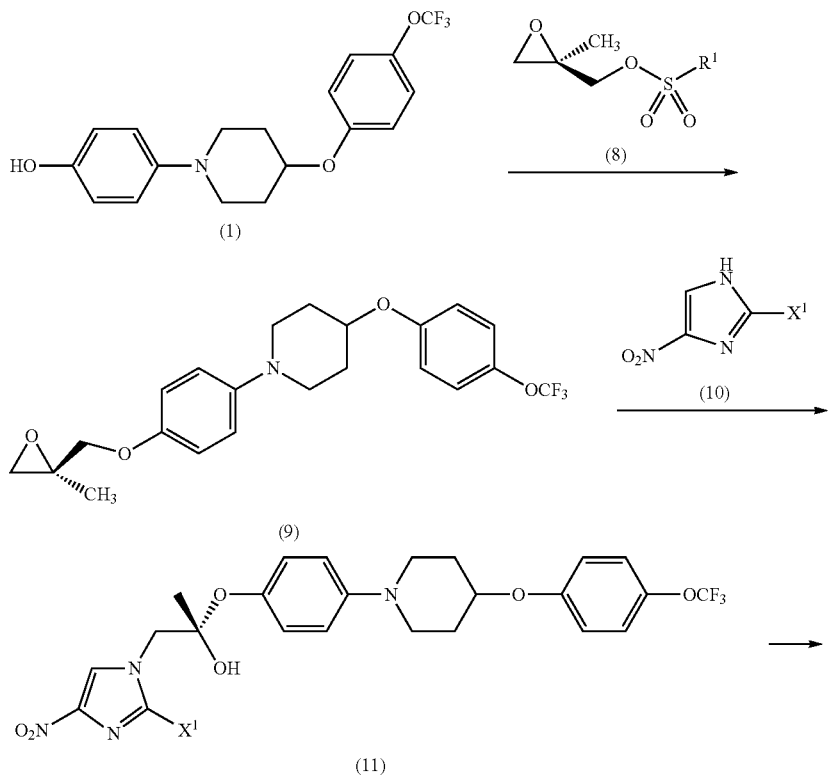

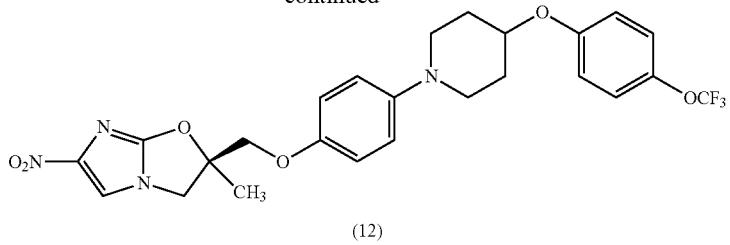

(12)

(wherein R[1] is $C_{1-6}$ alkyl optionally having one or more halogens, or phenyl optionally substituted with $C_{1-6}$ alkyl or nitro, and X[1] is halogen or nitro), wherein step (b) comprises the steps of:

(b1): reacting the compound of Formula (1) or a salt thereof with a compound represented by Formula (8) or a salt thereof in the presence of a phase transfer catalyst to produce the compound represented by Formula (9) or a salt thereof, which is a step for producing the compound represented by formula (9) or a salt thereof by using 1-(4-hydroxyphenyl)-4-(4-trifluoromethoxyphenoxy)piperidine or a salt thereof as a starting material;

(b2): reacting the compound of Formula (9) or a salt thereof with the compound represented by Formula (10) to produce the compound represented by Formula (11) or a salt thereof; and (b3): subjecting the compound represented by Formula (11) or a salt thereof to a ring closing reaction to produce the compound represented by Formula (12) or a salt thereof.

Item 9-1. The method according to Item 8, wherein the step (b1) for producing the compound represented by Formula (9) or a salt thereof by using 1-(4-hydroxyphenyl)-4-(4-trifluoromethoxyphenoxy)piperidine or a salt thereof as a starting material is replaced with a step shown below:

wherein the step comprises the steps of:

(c2): reacting the compound represented by Formula (14) with the compound represented by Formula (1) or a salt thereof to produce the compound represented by Formula (15) or a salt thereof; and (c3): epoxidating the compound represented by Formula (15) or a salt thereof to produce the compound represented by Formula (9) or a salt thereof.

Item 9-2. The method according to Item 8, wherein the step (b1) for producing the compound represented by Formula (9) or a salt thereof by using 1-(4-hydroxyphenyl)-4-(4-trifluoromethoxyphenoxy)piperidine or a salt thereof as a starting material is replaced with a step shown below:

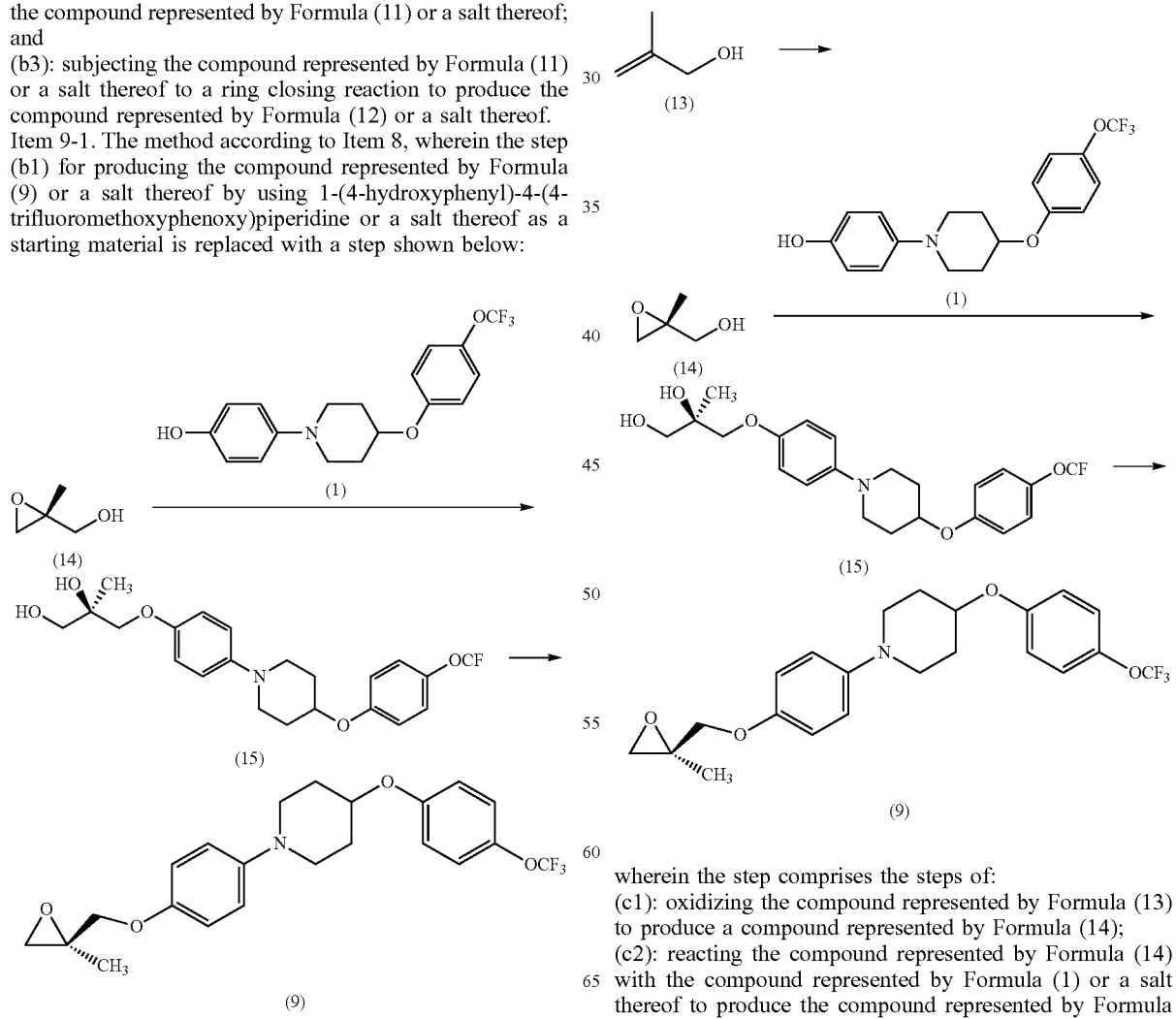

wherein the step comprises the steps of:

(c1): oxidizing the compound represented by Formula (13) to produce a compound represented by Formula (14);

(c2): reacting the compound represented by Formula (14) with the compound represented by Formula (1) or a salt thereof to produce the compound represented by Formula (15) or a salt thereof, and (c3): epoxidating the compound represented by Formula (15) or a salt thereof to produce the compound represented by Formula (9) or a salt thereof.

Item 10. A method for producing an anti-tubercular drug substance, comprising producing the compound represented by Formula (12) or a salt thereof by the method according to Item 7, 8, 9-1, or 9-2.

Item 11. A method for producing the compound represented by Formula (9) or a salt thereof by using 1-(4-hydroxyphenyl)-4-(4-trifluoromethoxyphenoxy)piperidine or a salt thereof as a starting material, the method comprising:

step (b1) according to Item 8, or steps (c2) and (c3) according to Item 9-1, or steps (c1), (c2), and (c3) according to Item 9-2.

Advantageous Effects of Invention

According to the production method of the present invention, 1-(4-hydroxyphenyl)-4-(4-trifluoromethoxyphenoxy) piperidine or a salt thereof can be produced with a high yield and high purity without necessitating complicated steps or using an expensive reagent or the like. Therefore, the production method of the present invention is industrially very useful.

DESCRIPTION OF EMBODIMENTS

Hereinafter, the production method of the present invention is described.

1. Production of Compound of Formula (1) or Salt Thereof

In the present invention, 1-(4-hydroxyphenyl)-4-(4-trifluoromethoxyphenoxy)piperidine represented by Formula (1):

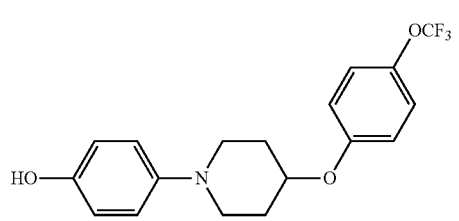

(1)

or a salt thereof is produced by heating hydroquinone represented by Formula (2):

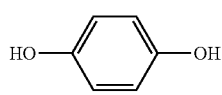

(2)

or a salt thereof and 4-(4-trifluoromethoxyphenoxy)piperidine represented by Formula (3):

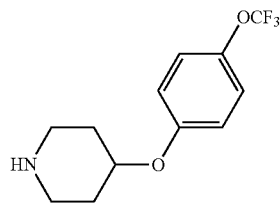

(3)

(hereinafter sometimes referred to as "a piperidine compound of Formula (3)")

or a salt thereof.

The hydroquinone or a salt thereof and the piperidine compound of Formula (3) or a salt thereof can be heated under catalyst-free and solvent-free conditions.

Heating is usually performed to such an extent that the reaction proceeds. For example, the heating is performed at or above the temperature at which a mixture of the hydroquinone or a salt thereof and the piperidine compound of Formula (3) or a salt thereof is dissolved (e.g., about 150° C. or higher). The upper limit is not particularly limited. The heating temperature is generally about 300° C. or less from the viewpoint of energy efficiency. More specifically, the heating temperature is about 150 to 300° C., more preferably about 150 to 250° C., and still more preferably about 180 to 210° C.

The compound of Formula (3) or a salt thereof, and the compound of Formula (2) (hydroquinone) or a salt thereof, which are reactants in the reaction, are both solids at room temperature. The reaction steps are not particularly limited. For example, the reaction can be performed by adding both reactants to a reactor kettle at room temperature, and then raising the temperature. Further, from the viewpoint of reaction efficiency, both reactants are preferably mixed (i.e., formed into a mixture) before reaction.

The heating time of the reaction is not particularly limited, as long as the reaction sufficiently proceeds. For example, heating for 1 hour or more is preferable. The upper limit of the heating time is usually 24 hours or less from the viewpoint of energy efficiency etc. More specifically, the reaction time is preferably 1 to 24 hours, and more preferably 1 to 6 hours or 2 to 3 hours.

When the temperature is within the above-mentioned range, the reaction usually is completed in about 1 to 3 hours. Byproduct formation can be prevented by performing the reaction within the temperature range described above and completing the reaction in a short period of time.

The reaction can also be performed in a suitable solvent. The solvent used in the reaction may be selected from a wide variety of known solvents that dissolve hydroquinone or a salt thereof and the piperidine compound of Formula (3) or a salt thereof, and that does not adversely affect the reaction. Examples include halogenated hydrocarbon solvents such as dichloromethane, chloroform, and carbon tetrachloride; lower alcohol solvents such as methanol, ethanol, and isopropyl alcohol; ketone solvents such as acetone and methyl ethyl ketone; ether solvents such as diethyl ether, dioxane, tetrahydrofuran, ethylene glycol monomethyl ether, and ethyleneglycol dimethyl ether; aromatic hydrocarbon solvents such as benzene, toluene, and xylene; ester solvents such as ethyl acetate and methyl acetate; acetonitrile; pyridine; 2,4,6-collidine; dimethyl sulfoxide; dimethylformamide; hexamethylphosphoric triamide; mixed solvents thereof; and the like.

The amount of hydroquinone or a salt thereof used is not particularly limited as long as the compound of Formula (1) or a salt thereof can be obtained. In terms of the yield, hydroquinone or a salt thereof is preferably used in an amount of 1.5 moles or more per mole of the piperidine compound of Formula (3) or a salt thereof. The upper limit is not particularly limited, and 10 moles or less is economical. More specifically, the amount of hydroquinone or a salt thereof used is preferably 1.5 to 10 moles, more preferably 2 to 10 moles, and still more preferably 2.5 to 10 moles, per mole of the piperidine compound of Formula (3) or a salt thereof. Not only in terms of the yield but also in terms of inhibiting impurity formation, hydroquinone or a salt thereof is preferably used in an amount within the above-mentioned range. In particular, in terms of the reaction rate, the amount of hydroquinone or a salt thereof is preferably 2 moles or more. Further, in terms of inhibiting impurity formation, the amount is preferably 2.5 moles or more.

In terms of preventing oxidation of the compound of Formula (1), the reaction is preferably performed under oxygen-free conditions. Specifically, the reaction is preferably performed in an inert atmosphere, such as nitrogen gas or argon gas. Known methods can be used to perform the reaction in an inert atmosphere.

When the reaction mixture is returned to room temperature after completion of the reaction, adding a solvent can prevent the residual hydroquinone etc. to be completely solidified in a reaction vessel. This facilitates subsequent steps, such as purification. When the method using a solvent is used, crystals of the reaction product obtained thereafter can have an improved color. Even if the solvent used in this step does not dissolve the reaction mixture, as long as the reaction mixture can be formed into a slurry by adding the solvent and stirring, subsequent steps can be performed without any difficulty. The solvent is not particularly limited. Examples include diphenyl ether, ethyl acetate, n-octyl acetate, mixed solvents thereof, and the like. These solvents can be used as is, as a solvent for the salt formation described below.

The 1-(4-hydroxyphenyl)-4-(4-trifluoromethoxyphenoxy)piperidine obtained by the reaction can, in general, be easily crystallized by dissolution in an appropriate solvent and salt formation by adding, for example, an acid compound. Examples of acid compounds include hydrochloric acid, hydrobromic acid, hydroiodic acid, sulfuric acid, nitric acid, phosphoric acid, formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, p-toluenesulfonic acid, glutamic acid, and the like. Among these, p-toluenesulfonic acid is preferable.

As a solvent in salt formation, a wide variety of known solvents can be used as long as they do not inhibit the reaction. Examples of such solvents include amide solvents such as N,N-dimethylformamide (DMF), N,N-dimethylacetamide, and N-methylpyrrolidone; aprotic polar solvents such as dimethylsulfoxide (DMSO) and acetonitrile; ketone solvents such as acetone and methyl ethyl ketone; hydrocarbon solvents such as benzene, toluene, xylene, tetralin, and liquid paraffin; alcoholic solvents such as methanol, ethanol, isopropanol, n-butanol, and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like. These solvents may contain water.

The salt of 1-(4-hydroxyphenyl)-4-(4-trifluoromethoxyphenoxy)piperidine obtained by the method of the present invention (preferably a salt of p-toluenesulfonic acid) can be further purified by a recrystallization method. The solvent used in recrystallization may be the same as the solvent used in salt formation.

The hydroquinone is an easily available compound. A commercially available product thereof can be used as is.

The salt of hydroquinone and the salt of 4-(4-trifluoromethoxyphenoxy)piperidine, which may be reactants of the reaction, are preferably those obtained by adding an acid compound to hydroquinone or 4-(4-trifluoromethoxyphenoxy)piperidine and forming a salt. Examples of the acid compound used in this reaction may be the same as those usable in the salt formation of 1-(4-hydroxyphenyl)-4-(4-trifluoromethoxyphenoxy)piperidine.

2. Production of Piperidine Compound of Formula (3)

The piperidine compound of Formula (3) used as a starting material is a known compound. The compound can be produced, for example, by the method shown in Reaction Scheme-1 below. A salt of each compound may be used as a reactant in each reaction in Reaction Scheme-1, as long as the salt does not significantly inhibit the reaction.

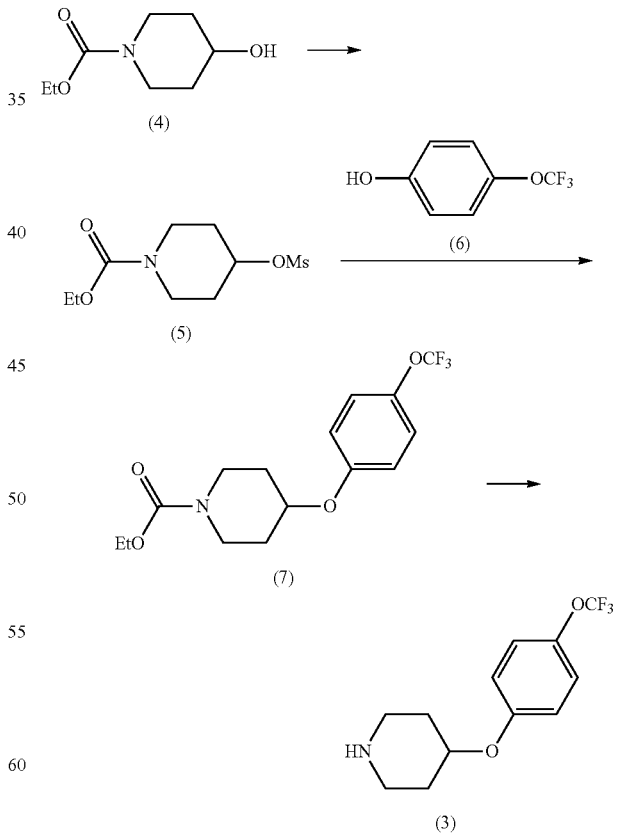

Reaction Scheme-1

(wherein Et represents ethyl and Ms represents methanesulfonyl).

The reaction leading from the compound represented by Formula (4) to the compound represented by Formula (5) is generally performed in an appropriate solvent in the presence of mesyl chloride, in the presence or absence of a basic compound.

A wide variety of known solvents can be used as the solvent, as long as they do not inhibit the reaction. Examples of such solvents include amide solvents such as N,N-dimethylformamide (DMF), N,N-dimethylacetamide, and N-methylpyrrolidone; aprotic polar solvents such as dimethylsulfoxide (DMSO) and acetonitrile; ketone solvents such as acetone and methyl ethyl ketone; hydrocarbon solvents such as benzene, toluene, xylene, tetralin, and liquid paraffin; alcoholic solvents such as methanol, ethanol, isopropanol, n-butanol, and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; and mixed solvents thereof.

Mesyl chloride is usually used in an amount of at least 1 mole or more, and preferably 1 to 5 moles, per mole of the compound represented by Formula (4).

A wide variety of known organic bases and inorganic bases can be used as the basic compound.

Examples of organic bases include metal alcoholates such as sodium methylate, sodium ethylate, sodium, and n-butoxide; pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene 7 (DBU), 1,4-diazabicyclo[2.2.2]octane (DABCO), 1,8-bis(dimethylamino)naphthalene, and the like.

Examples of inorganic bases include metal carbonates such as sodium carbonate, potassium carbonate, sodium hydrogen carbonate, potassium hydrogen carbonate, and cesium carbonate; metal hydroxides such as sodium hydroxide, potassium hydroxide, calcium hydroxide, and cesium hydroxide; metal hydrides such as sodium hydride and potassium hydride; phosphates such as tripotassium phosphate, dipotassium hydrogen phosphate, trisodium phosphate, and disodium hydrogen phosphate; alkali metals such as potassium and sodium; and the like. Examples of inorganic bases further include sodium amide in addition to those mentioned above.

These basic compounds are used singly, or in a combination of two or more.

The amount of the basic compound, if used, is usually at least 1 mole or more, and preferably 1 to 5 moles, per mole of the compound of Formula (4).

The reaction leading from the compound of Formula (4) to the compound of Formula (5) usually proceeds at −20 to 150° C., and preferably at about 0 to 120° C. The reaction is generally completed in about 5 minutes to about 10 hours.

The reaction between the compound of Formula (5) and the compound of Formula (6) is generally performed in an appropriate solvent in the presence of a phase-transfer catalyst in the presence or absence of a basic compound. This reaction synthesizes the compound of Formula (7).

A wide variety of known solvents can be used as the solvent, as long as they do not inhibit the reaction. Examples of such solvents include water; amide solvents such as N,N-dimethylformamide (DMF), N,N-dimethylacetamide, and N-methylpyrrolidone; aprotic polar solvents such as dimethylsulfoxide (DMSO) and acetonitrile; ketone solvents such as acetone and methyl ethyl ketone; hydrocarbon solvents such as benzene, toluene, xylene, tetralin, and liquid paraffin; alcohol solvents such as methanol, ethanol, isopropanol, n-butanol, and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like.

Examples of phase-transfer catalysts include quaternary ammonium salts, phosphonium salts, pyridinium salts, and the like.

Specific examples of quaternary ammonium salts include quaternary ammonium salts substituted with at least one substituent selected from the group consisting of linear or branched alkyl groups having 1 to 18 carbon atoms, phenylalkyl groups wherein the alkyl moiety is a linear or branched alkyl group having 1 to 6 carbon atoms, and phenyl, such as tetrabutylammonium chloride, tetrabutylammonium bromide, tetrabutylammonium fluoride, tetrabutylammonium iodide, tetrabutylammonium hydroxide, tetrabutylammonium hydrogen sulfate, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, and tetramethylammonium chloride.

Specific examples of phosphonium salts include phosphonium salts substituted with a linear or branched alkyl group having 1 to 18 carbon atoms or a substituted amino group, such as tetrabutylphosphonium chloride and tetrakis[tris(dimethylamino)phosphoranylideneamino]phosphonium chloride, and the like.

Examples of pyridinium salts substituted with a linear or branched alkyl group having 1 to 18 carbon atoms, such as 1-dodecanylpyridinium chloride.

These phase-transfers catalysts can be used singly, or in a combination of two or more.

The phase-transfer catalyst is usually used in an amount of 0.1 to 1 mole, and preferably 0.1 to 0.5 moles, per mole of the compound of Formula (6).

A wide variety of known organic bases and inorganic bases can be widely used as the basic compound.

Examples of organic bases include metal alcoholates such as sodium methylate, sodium ethylate, sodium, and n-butoxide; pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), 1,8-bis(dimethylamino)naphthalene, and the like.

Examples of inorganic bases include metal carbonates such as sodium carbonate, potassium carbonate, sodium hydrogen carbonate, potassium hydrogen carbonate, and cesium carbonate; hydroxides such as sodium hydroxide, potassium hydroxide, calcium hydroxide, and cesium hydroxide; hydrides such as sodium hydride and potassium hydride; phosphates such as tripotassium phosphate, dipotassium hydrogen phosphate, trisodium phosphate, and disodium hydrogen phosphate; alkali metals such as potassium and sodium; and the like. Examples of inorganic bases further include sodium amide in addition to those mentioned above.

These basic compounds are used singly, or in a combination of two or more.

The basic compound is usually used in an amount of at least 1 mole or more, and preferably 1 to 10 moles, per mole of the compound of Formula (6).

The reaction between the compound of Formula (5) and the compound of Formula (6) usually proceeds at 0 to 200° C., and preferably at about 0 to 150° C. The reaction is generally completed in about 5 minutes to about 10 hours.

The reaction leading from the compound of Formula (7) to the compound of Formula (3) is generally performed in a suitable inert solvent in the presence or absence of a basic compound.

A wide variety of solvents can be used as the solvent, as long as they do not inhibit the reaction. Examples of such solvents include water; amide solvents such as N,N-dimethylformamide (DMF), N,N-dimethylacetamide, and N-methylpyrrolidone; aprotic polar solvents such as dimethyl sulfoxide (DMSO) and acetonitrile; ketone solvents such as acetone and methyl ethyl ketone; hydrocarbon solvents such as benzene, toluene, xylene, tetralin, and liquid paraffin; alcohol solvents such as methanol, ethanol, isopropanol, n-butanol, and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like.

A wide variety of known organic bases and inorganic bases can be used as the basic compound.

Examples of organic bases include metal alcoholates such as sodium methylate, sodium ethylate, sodium, and n-butoxide; pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), 1,8-bis(dimethylamino)naphthalene, and the like.

Examples of inorganic bases include carbonates such as sodium carbonate, potassium carbonate, sodium hydrogen carbonate, potassium hydrogen carbonate, and cesium carbonate; hydroxides such as sodium hydroxide, potassium hydroxide, calcium hydroxide, and cesium hydroxide; hydrides such as sodium hydride and potassium hydride; phosphates such as tripotassium phosphate, dipotassium hydrogen phosphate, trisodium phosphate, and disodium hydrogen phosphate; alkali metals such as potassium and sodium; and the like. Examples of inorganic bases further include sodium amide in addition to those mentioned above.

These basic compounds are used singly, or in a combination of two or more.

The basic compound is usually used in an amount of at least 1 mole or more, and preferably 1 to 20 moles, per mole of the compound of Formula (7).

This reaction usually proceeds at 0 to 200° C., and preferably at about 0 to 150° C. The reaction is generally completed in about 5 minutes to about 10 hours.

3. Efficacy of the Compound of Formula (1)

1-(4-Hydroxyphenyl)-4-(4-trifluoromethoxyphenoxy)piperidine (compound of Formula (1)) or a salt thereof of the present invention is a compound useful as an intermediate in the synthesis of various medicaments (preferably antitubercular agents), agricultural chemicals, etc. This intermediate leads to delamanid (the compound of Formula (12)), which is useful as an antitubercular agent, in accordance with, for example, the method shown in Reaction Scheme-2 below. A salt of each compound may be used as a reactant in each reaction shown in Reaction Scheme-2, as long as the salt does not significantly inhibited the reaction.

Reaction Scheme-2

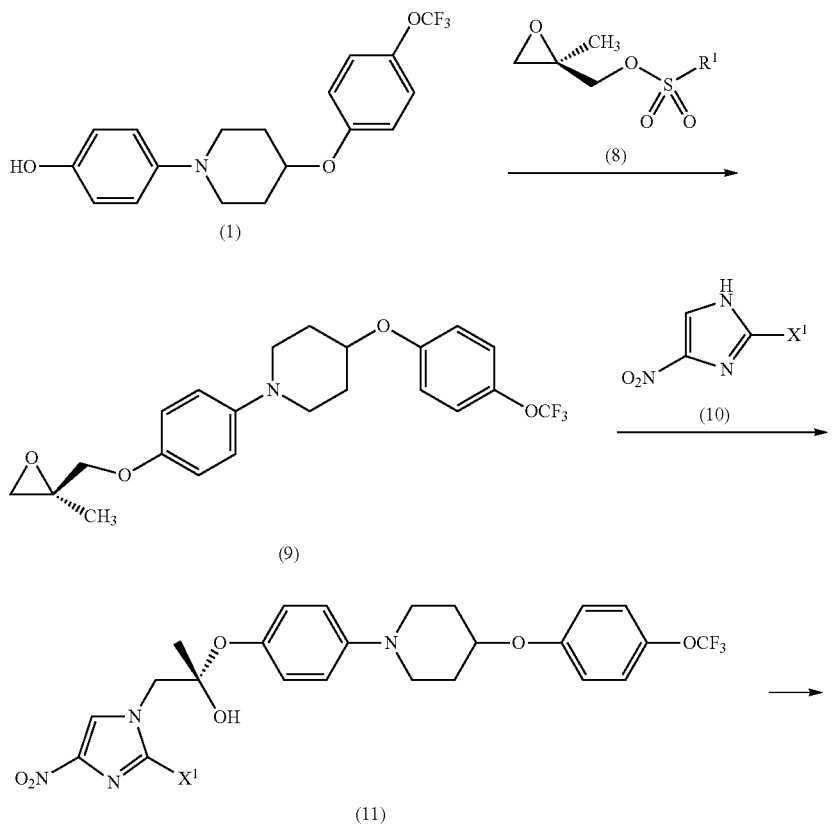

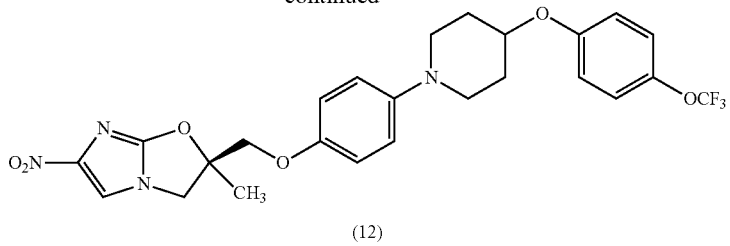

(12)

(wherein $R^1$ is $C_{1-6}$ alkyl optionally substituted with one or more halogens, or phenyl optionally substituted with $C_{1-6}$ alkyl or nitro, and $X^1$ is halogen or nitro).

Examples of halogens include fluorine, chlorine, bromine, iodine, and like atoms.

Examples of $C_{1-6}$ alkyl optionally substituted with one or more halogens include methyl, ethyl, trifluoromethyl, and the like.

Examples of phenyl optionally substituted with $C_{1-6}$ alkyl or nitro include phenyl, 4-tolyl, 2-tolyl, 4-nitrophenyl, 2-nitrophenyl, and the like.

$X^1$ is preferably a halogen. Chlorine is particularly preferable.

The reaction between the compound of Formula (1) and the compound of Formula (8) is generally performed in an appropriate inert solvent in the presence of a phase-transfer catalyst in the presence or absence of a basic compound. This reaction synthesizes the compound of Formula (9). In this reaction, it is also possible to use a salt of the compound of Formula (1).

A wide variety of solvents can be used as the solvent, as long as they do not inhibit the reaction. Examples of solvents include water; amide solvents such as N,N-dimethylformamide (DMF), and N,N-dimethylacetamide, and N-methylpyrrolidone; aprotic polar solvents such as dimethyl sulfoxide (DMSO) and acetonitrile; ketone solvents such as acetone and methyl ethyl ketone; hydrocarbon solvents such as benzene, toluene, xylene, tetralin, and liquid paraffin; alcohol solvents such as methanol, ethanol, isopropanol, n-butanol, and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like.

Examples of phase-transfer catalysts include quaternary ammonium salts, phosphonium salts, pyridinium salts, and the like.

Specific examples of quaternary ammonium salts include quaternary ammonium salts substituted with at least one substituent selected from the group consisting of linear or branched alkyl groups having 1 to 18 carbon atoms, phenylalkyl groups wherein the alkyl moiety is a linear or branched alkyl group having 1 to 6 carbon atoms, and phenyl, such as tetrabutylammonium chloride, tetrabutylammonium bromide, tetrabutylammonium fluoride, tetrabutylammonium iodide, tetrabutylammonium hydroxide, tetrabutylammonium hydrogen sulfate, tributylmethylammonium chloride, tributylbenzylammonium chloride, tetrapentylammonium chloride, tetrapentylammonium bromide, tetrahexylammonium chloride, benzyldimethyloctylammonium chloride, methyltrihexylammonium chloride, benzyldimethyloctadecanylammonium chloride, methyltridecanylammonium chloride, benzyltripropylammonium chloride, benzyltriethylammonium chloride, phenyltriethylammonium chloride, tetraethylammonium chloride, and tetramethylammonium chloride; and the like.

Specific examples of phosphonium salts include phosphonium salts substituted with a linear or branched alkyl group having 1 to 18 carbon atoms or a substituted amino group, such as tetrabutylphosphonium chloride and tetrakis[tris(dimethylamino)phosphoranylideneamino]phosphonium chloride; and the like.

Examples of pyridinium salts include pyridinium salts substituted with a linear or branched alkyl group having 1 to 18 carbon atoms, such as 1-dodecanylpyridinium chloride.

These phase-transfers catalysts are used singly, or in a combination of two or more.

The phase-transfer catalyst is usually used in an amount of 0.1 to 1 mole, and preferably 0.1 to 0.5 moles, per mole of the compound of Formula (1) or a salt thereof.

A wide variety of known organic bases and inorganic bases can be used as the basic compound.

Examples of organic bases include metal alcoholates such as sodium methylate, sodium ethylate, sodium, and n-butoxide; pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), 1,8-bis(dimethylamino)naphthalene, and the like.

Examples of inorganic bases include carbonates such as sodium carbonate, potassium carbonate, sodium hydrogen carbonate, potassium hydrogen carbonate, and cesium carbonate; hydroxides such as sodium hydroxide, potassium hydroxide, calcium hydroxide, and cesium hydroxide; hydrides such as lithium hydroxide, sodium hydride, and potassium hydride; phosphates such as tripotassium phosphate, dipotassium hydrogen phosphate, trisodium phosphate, and disodium hydrogen phosphate; alkali metals such as potassium and sodium; and the like. Examples of inorganic bases also include sodium amide, in addition to those mentioned above.

These basic compounds are used singly, or in a combination of two or more.

The basic compound is usually used in an amount of at least 1 mole or more, and preferably 1 to 10 moles, per mole of the compound of Formula (1) or a salt thereof.

The reaction between the compound of Formula (1) or a salt thereof and the compound of Formula (8) usually proceeds at 0 to 200° C., and preferably at about 0 to 150° C. The reaction is generally completed in about 5 minutes to about 10 hours.

The reaction between the compound of Formula (9) and the compound of Formula (10) is performed in an appropriate inert solvent, or without a solvent, in the presence or absence of a basic compound. This reaction synthesizes the compound of Formula (11).

A wide variety of solvents can be used as the solvent, as long as they do not inhibit the reaction. Examples of such solvents include water; amide solvents such as N,N-dimethylformamide (DMF), N,N-dimethylacetamide, and N-methylpyrrolidone; aprotic polar solvents such as dimethylsulfoxide (DMSO) and acetonitrile; ketone solvents such as acetone and methyl ethyl ketone; hydrocarbon solvents such as benzene, toluene, xylene, tetralin, and liquid paraffin; alcoholic solvents such as methanol, ethanol, isopropanol, n-butanol, and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like.

A wide variety of known organic bases and inorganic bases can be used as the basic compound.

Examples of the organic base include metal alcoholates such as sodium methylate, sodium ethylate, sodium, and n-butoxide; pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), 1,8-bis(dimethylamino)naphthalene, and the like.

Examples of inorganic bases include carbonates such as sodium carbonate, potassium carbonate, sodium hydrogen carbonate, potassium hydrogen carbonate, and cesium carbonate; hydroxides such as sodium hydroxide, potassium hydroxide, calcium hydroxide, and cesium hydroxide; hydrides such as sodium hydride and potassium hydride; phosphates such as tripotassium phosphate, dipotassium hydrogen phosphate, trisodium phosphate, and disodium hydrogen phosphate; alkali metals such as potassium and sodium; and the like. Examples of inorganic bases include sodium amide and the like, in addition to those mentioned above.

Such basic compounds are used singly, or in a combination of two or more.

The basic compound is usually used in an amount of at least 1 mole or more, and preferably 1 to 10 moles, per mole of the compound of Formula (10).

This reaction usually proceeds at 0 to 200° C., and preferably at about 0 to 150° C. The reaction is generally completed in about 5 minutes to about 40 hours.

The compound of Formula (12) is produced by subjecting the compound of Formula (11) to a ring closure reaction. The ring closure reaction is performed by dissolving the compound represented by Formula (11) in a reaction solvent, adding a basic compound, and stirring at a predetermined temperature.

As the reaction solvent and basic compound, the same reaction solvent and basic compound as used in the reaction between the compound of Formula (9) and the compound of Formula (10) can be used.

The basic compound is usually used in an amount of 1 mole or more (1 mole to an excess moles), preferably 1 to 5 moles, and more preferably 1 to 2 moles, per mole of the compound of Formula (11).

The reaction temperature of the ring closure reaction is usually −20 to 150° C., preferably −10 to 120° C., and more preferably −10 to 100° C. The reaction time is usually 10 minutes to 48 hours, preferably 10 minutes to 24 hours, and more preferably 20 minutes to 4 hours.

In the present invention, the compound of Formula (11) obtained by a reaction between the compound of Formula (9) and the compound of Formula (10) can be subjected to a ring closure reaction as is without isolation. The target compound represented by Formula (12) can be produced in this manner, as well.

The compound of Formula (9) can also be produced by using the compound of Formula (1) or a salt thereof in accordance with the method shown in Reaction Scheme-3 below. The compound of Formula (9) can be converted to the compound of Formula (12) by the same procedure as described above. In this method, a salt of each compound can be used as a reactant in each reaction shown in Reaction Scheme-3, as long as the salt does not significantly inhibit the reaction.

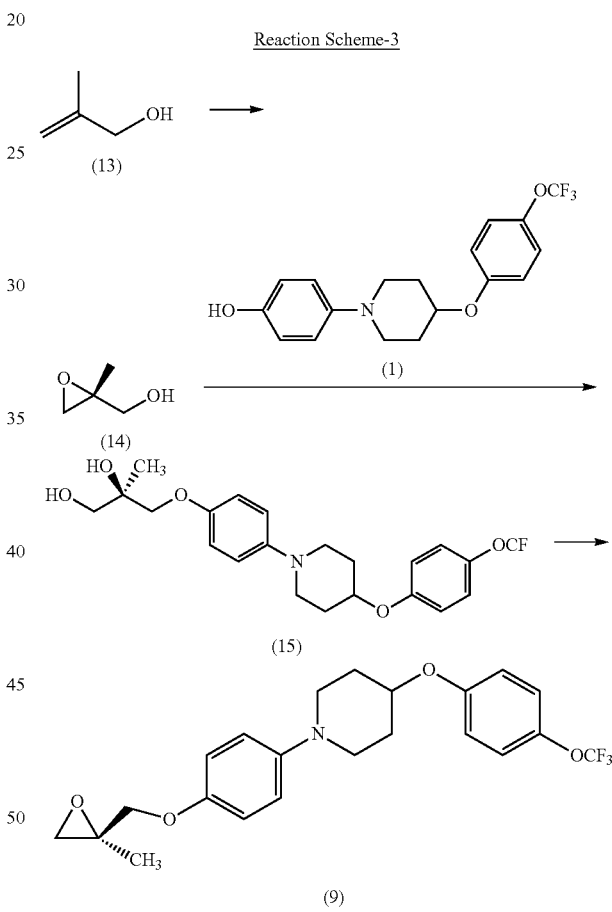

Reaction Scheme-3

The compound of Formula (15) can be oxidized into the compound of Formula (9). The compound of Formula (15) can be produced by reacting the compound of Formula (14) with the compound of Formula (1). The compound of Formula (14) can be prepared by oxidizing (more specifically, asymmetrically epoxidating) the compound of Formula (13) (2-methylallyl alcohol).

The oxidation reaction of the compound of Formula (13) is performed in an appropriate solvent in the presence of a dextrorotatory optically active compound using an oxidizing agent. The oxidation reaction is preferably performed by Sharpless-Katsuki asymmetric epoxidation.

A wide variety of peroxides can be used as the oxidizing agent. Examples include cumene hydroperoxide, tert-butyl peroxide, trityl hydroperoxide, and the like.

Examples of the solvent include alcohols such as methanol, ethanol, and isopropanol; aromatic hydrocarbons such as benzene, toluene, and xylene; halogenated hydrocarbons such as dichloromethane, dichloroethane, chloroform, and carbon tetrachloride; ethers such as diethyl ether, dimethoxyethane, dioxane, tetrahydrofuran, and diglyme; saturated hydrocarbons such as n-hexane, n-butane, and cyclohexane; ketones such as acetone and methyl ethyl ketone; and polar solvents such as N,N-dimethylformamide, N,N-dimethylacetamide, N-methylpyrrolidone, dimethyl sulfoxide, hexamethylphosphoric triamide, and acetonitrile; mixed solvents thereof; and the like.

Examples of dextrorotatory optically active compounds include dextrorotatory optically active acid or alkyl esters thereof, such as D-(−)-dimethyl tartrate, D-(−)-diethyl tartrate, D-(−)-diisopropyl tartrate, D-(−)-dibutyl tartrate, (D)-(−)-tartaric acid, (D)-(−)-di-p-toluoyltartaric acid, (D)-(−)-malic acid, (D)-(−)-mandelic acid, and (D)-(−)-camphor 10-sulfonic acid. Among these, tartaric acid dialkyl esters such as D-(−)-dimethyl tartrate, D-(−)-diethyl tartrate, D-(−)-diisopropyl tartrate, and D-(−)-dibutyl tartrate, are preferable.

The oxidizing agent is usually used in an amount of at least about 1 mole, and preferably about 1 to 3 moles, per mole of the compound (13).

The optically active compound is usually used in an amount of about 0.01 to 1 mole, and preferably about 0.01 to 0.5 moles, per mole of the compound (13).

The oxidation reaction of the compound (13) is usually performed at about −50° C. to about room temperature, and preferably about −30° C. to about room temperature. The reaction is generally completed in about 1 to 30 hours.

When the oxidation reaction of compound (13) is performed, adding a reaction accelerator to the reaction system is preferable. Examples of reaction accelerators include titanium alkoxides such as titanium tetraisopropoxide, titanium tetraethoxide, titanium tetramethoxide, and titanium tetrabutoxide; molecular sieves such as molecular sieve 5A, molecular sieve 4A, and molecular sieve 3A; and the like. These reaction accelerators are used singly, or in a combination of two or more. A combination of at least one titanium alkoxide and at least one molecular sieve is particularly preferable. Titanium alkoxide is usually used in an amount of about 0.01 to 1 mole, and preferably about 0.01 to 0.5 moles, per mole of the compound (13). The molecular sieve is usually used in an amount of 0.1 to 1 time the weight of the compound (13).

After completion of the reaction, dimethyl sulfoxide (DMSO) is preferably added to the reaction system to remove the oxidizing agent. The amount of DMSO used can be properly selected according to the amount of the residual oxidizing agent. The reaction between the compound of Formula (14) and the compound of Formula (1) or a salt thereof can generally be performed in a suitable solvent in the presence of a basic compound. This reaction synthesizes the compound of formula (15) or a salt thereof. An embodiment of using a salt of the compound of Formula (1) will be described below. Using a p-toluenesulfonic acid salt of the compound of Formula (1) is particularly preferable.

A wide variety of solvents can be used as the solvent, as long as they do not inhibit the reaction. Examples of such solvents include water; amide solvents such as N,N-dimethylformamide (DMF), N,N-dimethylacetamide, and N-methylpyrrolidone; aprotic polar solvents such as dimethyl sulfoxide (DMSO) and acetonitrile; ketone solvents such as acetone and methyl ethyl ketone; hydrocarbon solvents such as benzene, toluene, xylene, tetralin, and liquid paraffin; alcoholic solvents such as methanol, ethanol, isopropanol, n-butanol, and tert-butanol; ether solvents such as tetrahydrofuran (THF), dioxane, dipropyl ether, diethyl ether, diphenylether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like.

A wide variety of known organic bases and inorganic bases can be used as the basic compound.

Examples of organic bases include metal alcoholates such as sodium methylate, sodium ethylate, sodium, and n-butoxide; pyridine, imidazole, N-ethyldiisopropylamine, dimethylaminopyridine, triethylamine, trimethylamine, dimethylaniline, N-methylmorpholine, 1,5-diazabicyclo[4.3.0] nonene-5 (DBN), 1,8-diazabicyclo[5.4.0]undecene-7 (DBU), 1,4-diazabicyclo[2.2.2]octane (DABCO), 1,8-bis (dimethylamino)naphthalene, and the like.

Examples of inorganic bases include metal carbonates (such as sodium carbonate, potassium carbonate, sodium hydrogen carbonate, potassium hydrogen carbonate, and cesium carbonate); metal hydroxides (such as sodium hydroxide, potassium hydroxide, calcium hydroxide, and cesium hydroxide); metal hydrides (such as lithium hydroxide, sodium hydride, and potassium hydride); metal phosphates (such as tripotassium phosphate, dipotassium hydrogen phosphate, trisodium phosphate, and disodium hydrogen phosphate); alkali metals (such as potassium and sodium); and the like. Examples of inorganic bases include sodium amide and the like, in addition to those mentioned above.

These basic compounds are used singly, or in a combination of two or more.

The basic compound is usually used in an amount of at least 0.5 or 1 mole or more, and preferably 1 to 10 moles, per mole of the compound of Formula (1) or a salt thereof.

The reaction between the compound of Formula (14) and the compound of Formula (1) or a salt thereof (the salt is preferably a p-toluenesulfonic acid salt (HTP-TSA)) usually proceeds at 0 to 200° C., and preferably at about 0 to 150° C. The reaction is generally completed in about 5 minutes to about 10 hours.

Examples of salts of the compound of Formula (1) include salts of inorganic acids and salts of organic acids. Specific examples of inorganic acid salts include hydrochloric acid salts, hydrobromic acid salts, hydroiodic acid salts, sulfonic acid salts, nitric acid salts, phosphoric acid salts, and the like. Examples of organic acid salts include formic acid salts, acetic acid salts, propionic acid salts, oxalic acid salts, malonic acid salts, succinic acid salts, fumaric acid salts, maleic acid salts, lactic acid salts, malic acid salts, citric acid salts, tartaric acid salts, carbonic acid salts, picric acid salts, methanesulfonic acid salts, ethanesulfonic acid salts, p-toluenesulfonic acid salts, glutamic acid salts, and the like. p-Toluenesulfonic acid salts are particularly preferable.

The compound of Formula (15) obtained by this reaction can be easily crystallized by dissolving the compound in a suitable solvent and adding an acid compound, such as p-toluenesulfonic acid, to form a salt. Examples of the acid compound may be the same as those usable in the salt formation of 1-(4-hydroxyphenyl)-4-(4-trifluoromethoxyphenoxy)piperidine described above. Examples of salts of other compounds referred to in this specification also include salts formed by adding such an acid compound to other compounds, unless otherwise specified.

A wide variety of known solvents can be used as the solvent in salt formation, as long as they do not inhibit the reaction. Examples of such solvents include amide solvents such as N,N-dimethylformamide (DMF), N,N-dimethylacetamide, and N-methylpyrrolidone; aprotic polar solvents such as dimethylsulfoxide (DMSO) and acetonitrile; ketone solvents such as acetone and methyl ethyl ketone; hydrocarbon solvents such as benzene, toluene, xylene, tetralin and liquid paraffin; alcohol solvents such as methanol, ethanol, isopropanol, n-butanol and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like. These solvents may contain water, if necessary.

At least one member selected from the group consisting of toluene and isopropanol is particularly preferable. A mixed solvent of toluene and isopropanol is more preferable. When the phases are separated after the reaction, the phase separation is performed using toluene and water. After an aqueous layer is removed, isopropanol (and toluene, if necessary) is added to thereby easily form a salt and achieve recrystallization as described below.

The salt (preferably p-toluenesulfonic acid salt) of the compound of Formula (15) obtained by this method can be further purified by a recrystallization method. The solvent used in the recrystallization may be the same as that used in salt formation.

The compound of Formula (9) can be produced by epoxidating the compound of Formula (15) (or a salt thereof). The epoxidation can be performed, for example, by reacting the compound of Formula (15) or a salt thereof in a suitable solvent in the presence of an organic sulfonic acid halide in the presence or absence of a basic compound.

A wide variety of known solvents can be used as the solvent, as long as they do not inhibit the reaction. Examples of such solvents include amide solvents such as N,N-dimethylformamide (DMF), N,N-dimethylacetamide, and N-methylpyrrolidone; aprotic polar solvents such as dimethylsulfoxide (DMSO) and acetonitrile; ketone solvents such as acetone and methyl ethyl ketone; hydrocarbon solvents such as benzene, toluene, xylene, tetralin, and liquid paraffin; alcohol solvents such as methanol, ethanol, isopropanol, n-butanol, and tert-butanol; ether solvents such as tetrahydrofuran (THF), dioxane, dipropyl ether, diethyl ether, diphenyl ether, monoglyme, diglyme, and cyclopentylmethyl ether; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like. Among these, cyclopentylmethyl ether, methanol, and N,N-dimethylformamide (DMF) are preferable.

Examples of organic sulfonic acid halides include halides of methanesulfonic acid, p-toluenesulfonic acid, trifluoromethanesulfonic acid, (ortho-, meta-, or para-) nitrobenzene sulfonic acid, 2,4,6-trimethyl benzenesulfonic acid, or 2,4,6-triisopropylbenzenesulfonic acid. Among these, mesyl chloride (methanesulfonic acid chloride) is preferable.

The organic sulfonic acid halide is usually used in an amount of at least 1 mole or more, and preferably 1 to 5 moles, per mole of the compound of Formula (15) or a salt thereof.

A wide variety of known organic bases and inorganic bases can be used as the basic compound.

Examples of organic bases include metal alcoholates such as sodium methylate, sodium ethylate, sodium, and n-butoxide; pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO), 1,8-bis(dimethylamino)naphthalene, and the like.

Examples of inorganic bases include carbonates such as sodium carbonate, potassium carbonate, sodium hydrogen carbonate, potassium hydrogen carbonate, and cesium carbonate; metal hydroxides such as sodium hydroxide, potassium hydroxide, calcium hydroxide, and cesium hydroxide; metal hydrides such as sodium hydride and potassium hydride; phosphates such as tripotassium phosphate, dipotassium hydrogen phosphate, trisodium phosphate, and disodium hydrogen phosphate; alkali metals such as potassium and sodium; and the like. Examples of inorganic bases include sodium amide and the like in addition to those mentioned above.

These basic compounds are used singly, or in a combination of two or more.

The amount of basic compound, if used, is usually at least 1 mole or more, and preferably 1 to 5 moles, per mole of the compound of Formula (15) or a salt thereof.

The epoxidation usually proceeds at −20 to 150° C., and preferably at about 0 to 120° C. The reaction is generally completed in about 5 minutes to about 10 hours.

In the above method, the compound of Formula (15) or a salt thereof reacts with an organic sulfonic acid halide, and a hydroxyl group and an organic sulfonyloxy group in the compound obtained by the reaction are reacted to effect epoxidation, thus forming the compound of Formula (9).

The compound of Formula (9) can be easily crystallized by dissolving the compound in a suitable solvent and adding an acid compound, such as p-toluenesulfonic acid, to form a salt. Examples of the acid compound include the same as acid compounds usable in the salt formation of 1-(4-hydroxyphenyl)-4-(4-trifluoromethoxyphenoxy)piperidine.

A wide variety of known solvents can be used as the solvent for salt formation, as long as they do not inhibit the reaction. Examples of such solvents include amide solvents such as N,N-dimethylformamide (DMF), N,N-dimethylacetamide, and N-methylpyrrolidone; aprotic polar solvents such as dimethylsulfoxide (DMSO) and acetonitrile; ketone solvents such as acetone and methyl ethyl ketone; hydrocarbon solvents such as benzene, toluene, xylene, tetralin, and liquid paraffin; alcohol solvents such as methanol, ethanol, isopropanol, n-butanol, and tert-butanol; ether solvents such as tetrahydrofuran (THF), dioxane, dipropyl ether, diethyl ether, diphenyl ether, monoglyme, and diglyme; ester solvents such as methyl acetate, ethyl acetate, n-propyl acetate, n-butyl acetate, tert-butyl acetate, n-pentyl acetate, n-octyl acetate, methyl propionate, ethyl propionate, n-propyl propionate, n-butyl propionate, and tert-butyl propionate; mixed solvents thereof; and the like. These solvents may contain water, if necessary. Among these, isopropanol is preferable.

The salt of the compound of Formula (9) obtained by this method (preferably a p-toluenesulfonic acid salt) can be further purified by a recrystallization method. The solvent used in the recrystallization may be the same as the solvent used in the salt formation.

Each target compound obtained in each step can be isolated and purified from the reaction mixture by, for example, separating, after cooling, the reaction mixture into a crude reaction product by isolation procedures such as filtration, concentration, and extraction; and subjecting the crude reaction product to usual purification procedures such as column chromatography and recrystallization.

EXAMPLES

The present invention is described in further detail with reference to Reference Examples and Examples. However, the scope of the invention is not limited to these Examples.

Preparation of 4-(4-trifluoromethoxyphenoxy)piperidine

Reference Example 1

9.72 kg of ethyl 4-hydroxy-1-piperidinecarboxylate and 10.0 L of triethylamine were dissolved in 15.0 L of toluene, and the resulting solution was cooled to 10° C. or less. After 7.07 kg of mesyl chloride was added dropwise to this solution at 25° C. or less, stirring was further performed at 25° C. or less for 1 hour. Subsequently, 5.00 kg of 4-trifluoromethoxyphenol, 10 L of toluene, 17.7 L of a 25% aqueous sodium hydroxide solution, and 6.24 kg of a 50% tetra-n-butyl ammonium chloride aqueous solution were added to the reaction solution. The resulting mixture was refluxed for 2 hours (internal temperature: 88° C.). The reaction mixture was then cooled, and an aqueous layer was removed. The obtained organic layer was washed with 10 L of water. Subsequently, 14.2 kg of potassium hydroxide and 10 L of ethanol were added to the washed reaction mixture. The resulting mixture was refluxed for 4 hours (internal temperature: 98° C.). After cooling, the concentration was performed under reduced pressure. After 50 L of toluene was added to the concentrated residue, the organic layer was washed with 25 L of water, 25 L of brine, and 31 L of an aqueous ammonium chloride solution. The toluene solution after washing was concentrated under reduced pressure. After 5 L of isopropyl alcohol, 50 L of water, and 2.5 L of a 25% aqueous sodium hydroxide solution were added to the concentrated residue and a homogeneous solution was formed, the solution was cooled to 10° C. or less. After crystal precipitation, the reaction mixture was stirred at 10° C. or less for 1 hour, and the precipitate was then filtered. The crystals were washed with 15 L of water. The obtained crystals were dried in air to obtain 6.67 kg of 4-(4-trifluoromethoxyphenoxy)piperidine (isolation yield: 90.9%).

$^1$H-NMR (300 MHz, CDCl$_3$) δ ppm: 1.41 (2H, dddd), 1.90 (2H, m), 2.55 (2H, ddd), 2.92 (2H, ddd), 3.33 (1H, brs), 4.39 (1H, tt), 7.03 (2H, d), 7.25 (2H, d)

Preparation of 1-(4-hydroxyphenyl)-4-(4-trifluoromethoxyphenoxy)piperidine

Example 1

6.28 g of 4-(4-trifluoromethoxyphenoxy)piperidine and 2.65 g (1.0-fold equivalent) of hydroquinone were placed in a reaction vessel. After purging with nitrogen, stirring was performed at 195 to 210° C. for 2 hours. The conversion rate determined by HPLC after the reaction was 49.5%. After ethyl acetate was added to the reaction mixture and a homogeneous solution was formed, 5.02 g (1.1-fold equivalents) of p-toluenesulfonic acid monohydrate was added to the solution. After stirring at room temperature for 1 hour, the precipitate was filtered and washed with ethyl acetate. The obtained crude crystals were recrystallized in a mixture of 14 ml of ethyl acetate and 2.8 ml of water. The precipitate was filtered and washed with water, and then with ethyl acetate. The obtained crystals were dried in air to give 3.34 g of 1-(4-hydroxyphenyl)-4-(4-trifluoromethoxyphenoxy)piperidine p-toluenesulfonate (isolation yield: 26.4%, purity: 97.41%).

$^1$H-NMR (300 MHz, DMSO-d6) δ ppm: 1.9-2.2 (2H, br), 2.27 (3H, s), 2.2-2.4 (2H, br), 3.62 (2H, br), 4.77 (1H, br), 6.90 (2H, d, J=8.9 Hz), 7.11 (2H, d, J=7.8 Hz), 7.1-7.2 (2H, m), 7.32 (2H, d, J=8.9 Hz), 7.45-7.55 (2H, m), 7.49 (2H, d, J=7.9 Hz).

Example 2

2.00 g of 4-(4-trifluoromethoxyphenoxy)piperidine and 1.01 g (1.2-fold equivalent) of hydroquinone were placed in a reaction vessel. After purging with nitrogen, stirring was performed at 215 to 225° C. for 2 hours. The conversion rate determined by HPLC after the reaction was 52.9%.

Example 3

6.28 g of 4-(4-trifluoromethoxyphenoxy)piperidine and 3.18 g (1.2-fold equivalent) of hydroquinone were placed in a reaction vessel. After purging with nitrogen, stirring was performed at 195 to 210° C. for 2 hours. The conversion rate determined by HPLC after the reaction was 62.8%. After ethyl acetate was added to the reaction mixture, 5.02 g (1.1-fold equivalents) of p-toluenesulfonic acid monohydrate was added thereto. After stirring at room temperature for 1 hour, the precipitate was filtered and washed with ethyl acetate. The obtained crude crystals were recrystallized with a mixture of 80 ml of ethyl acetate and 16 ml of water. The precipitate was filtered and washed with water, and then with ethyl acetate. The obtained crystals were dried in air to give 4.54 g of 1-(4-hydroxyphenyl)-4-(4-trifluoromethoxyphenoxy)piperidine p-toluenesulfonate (isolation yield: 35.9%, purity: 99.75%).

Example 4

6.28 g of 4-(4-trifluoromethoxyphenoxy)piperidine and 3.97 g (1.5-fold equivalents) of hydroquinone were placed in a reaction vessel. After purging with nitrogen, stirring was performed at 195 to 210° C. for 2 hours. The conversion rate determined by HPLC after the reaction was 74.7%. After ethyl acetate was added to the reaction mixture and a homogeneous solution was formed, 5.02 g (1.1-fold equivalents) of p-toluenesulfonic acid monohydrate was added to the solution. After stirring at room temperature for 1 hour, the precipitate was filtered and washed with ethyl acetate. The obtained crude crystals were washed with a mixture of 80 ml of ethyl acetate and 16 ml of water. The precipitate was filtered, and washed with water and ethyl acetate. The obtained crystals were dried in air to give 6.02 g of 1-(4-hydroxyphenyl)-4-(4-trifluoromethoxyphenoxy)piperidine p-toluenesulfonate (isolation yield: 47.7%, purity: 99.89%).

Example 5

15.0 g of 4-(4-trifluoromethoxyphenoxy)piperidine and 15.8 g (2.5-fold equivalents) of hydroquinone were placed in a reaction vessel. After purging with nitrogen, stirring was performed under nitrogen flow at 195 to 210° C. for 2 hours. The conversion rate determined by HPLC after the reaction was 96.1%. After diphenylether and ethyl acetate were added to the reaction mixture and a homogeneous solution was formed, 12.0 g (1.1-fold equivalents) of p-toluenesulfonic acid monohydrate was added. After stirring at room temperature for 1 hour, the precipitate was filtered and washed with ethyl acetate. The obtained crude crystals (purity: 98.4%) were recrystallized in a mixture of 300 ml of ethyl acetate and 60 ml of water. The precipitate was filtered and washed with water, and then with ethyl acetate. The obtained crystals were dried in air to give 25.7 g of 1-(4-hydroxyphenyl)-4-(4-trifluoromethoxyphenoxy)piperidine p-toluenesulfonate (isolation yield: 85.3%, purity: 99.85%).

Example 6

15.0 g of 4-(4-trifluoromethoxyphenoxy)piperidine and 15.8 g (2.5-fold equivalents) of hydroquinone were placed in a reaction vessel. After purging with nitrogen, stirring was performed under nitrogen flow at 195 to 210° C. for 2 hours. The conversion rate determined by HPLC after the reaction was 97.5%. N-octyl acetate and ethyl acetate were added to the reaction mixture, and a homogeneous solution was formed. Subsequently, 12.0 g (1.1-fold equivalents) of p-toluenesulfonic acid monohydrate was added to the solution. After stirring at room temperature for 1 hour, the precipitate was filtered and washed with ethyl acetate. The obtained crystals were dried in air to give 28.6 g of 1-(4-hydroxyphenyl)-4-(4-trifluoromethoxyphenoxy)piperidine p-toluenesulfonate (isolation yield: 94.8%, purity: 99.09%). Melting point: 218.9 to 219.6° C.

Example 7

5.00 g of 4-(4-trifluoromethoxyphenoxy)piperidine and 6.32 g (3.0-fold equivalents) of hydroquinone were placed in a reaction vessel. After purging with nitrogen, stirring was performed under nitrogen flow at 155 to 165° C. for 14 hours. The conversion rate determined by HPLC after the reaction was 89.7%. After N-octyl acetate and ethyl acetate were added to the reaction mixture and a homogeneous solution was formed, 4.00 g (1.1-fold equivalents) of p-toluenesulfonic acid monohydrate was added. Stirring was performed at room temperature for 1 hour. The precipitate was filtered and washed with ethyl acetate. The obtained crystals were dried in air to give 8.47 g of 1-(4-hydroxyphenyl)-4-(4-trifluoromethoxyphenoxy)piperidine p-toluenesulfonate (isolation yield: 84.2%, purity: 94.36%). Melting point: 218.9 to 219.6° C.

Example 8

15.0 g of 4-(4-trifluoromethoxyphenoxy)piperidine and 19.0 g (3.0-fold equivalents) of hydroquinone were placed in a reaction vessel. After purging with nitrogen, stirring was performed under nitrogen flow at 195 to 210° C. for 1.5 hours. The conversion rate determined by HPLC after the reaction was 97.2%. After diphenylether and ethyl acetate were added to the reaction mixture and a homogeneous solution was formed, 12.0 g (1.1-fold equivalents) of p-toluenesulfonic acid monohydrate was added to the solution. The resulting mixture was stirred at room temperature for 30 minutes, and further stirred at 10° C. or less for 30 minutes. The precipitate was filtered and washed with ethyl acetate. The obtained crude crystals (purity: 99.1%) was washed with a mixture of 300 ml of ethyl acetate and 60 ml of water. The precipitate was filtered and washed with water, and then with ethyl acetate. The obtained crystals were dried in air to give 26.8 g of 1-(4-hydroxyphenyl)-4-(4-trifluoromethoxyphenoxy)piperidine p-toluenesulfonate (isolation yield: 88.8%, purity: 99.96%). Melting point: 218.9 to 219.6° C.

Example 9

12.0 kg of 4-(4-trifluoromethoxyphenoxy)piperidine and 12.6 (2.5-fold equivalents) of hydroquinone were placed in a reaction vessel. After purging with nitrogen, stirring was performed under nitrogen flow at 195 to 210° C. for 2 hours. The conversion rate determined by HPLC after the reaction was 95.6%. After diphenylether and ethyl acetate were added to the reaction mixture and a homogeneous solution was formed, 9.61 kg (1.1-fold equivalents) of p-toluenesulfonic acid monohydrate was added to the solution. Stirring was performed at 10° C. to room temperature for 1 hour. The precipitate was filtered and washed with ethyl acetate. The obtained crude crystals (purity: 96.8%) were recrystallized in a mixture of 240 L of ethyl acetate and 48 L of water. The precipitate was filtered and washed with water, and then with ethyl acetate. The obtained crystals were dried in air to give 21.1 kg of 1-(4-hydroxyphenyl)-4-(4-trifluoromethoxyphenoxy)piperidine p-toluenesulfonate (isolation yield: 87.7%, purity: 99.82%).

Production of 1-(4-hydroxyphenyl)-4-(4-trifluoromethoxyphenoxy)piperidine

Reference Example 2

90.0 g of 4-(4-trifluoromethoxyphenoxy)piperidine, 62.6 g of 4-bromophenol, 77.0 mg of palladium acetate (II), 360 mg of tri-t-butylphosphonium tetraphenylborate, 76 g of sodium t-butoxide, and 450 ml of toluene were added. After purging with nitrogen, a reaction was allowed to proceed at 90° C. or more for 2 hours. After the reaction mixture was cooled, 33.5 ml of hydrochloric acid, 6.3 g of ascorbic acid, and 18 g of silica gel were added and stirring was performed at 60° C. for 30 minutes. After stirring, the insoluble matter was removed by filtration and 270 ml of water was added to the filtrate. The resulting mixture was separated into layers. After the organic layer was concentrated, 900 ml of ethyl acetate and 72.1 g of p-toluenesulfonic acid monohydrate were added to the concentrated residue. The resulting mixture was stirred at room temperature for 30 minutes. After stirring, 180 ml of water and 90 ml of methanol were added, and the reaction mixture was dissolved under reflux. After confirming the dissolution, the solution was cooled, and stirring was performed at 10° C. or less for 1 hour. After stirring, the precipitate was filtered, washed with 270 ml of water and 270 ml of ethyl acetate, and then dried in air to give 157.4 g of 1-(4-hydroxyphenyl)-4-(4-trifluoromethoxyphenoxy)piperidine p-toluenesulfonate (isolation yield: 87.0%).

Production of (2R)-2-methyl-6-nitro-2-{4-[4-(4-trifluoromethoxyphenoxy)piperidin-1-yl]phenoxymethyl}-2,3-dihydroimidazo[2,1-b]oxazole Example 10

120 kg of 1-(4-hydroxyphenyl)-4-(4-trifluoromethoxyphenoxy)piperidine, 20.1 kg of lithium hydroxide monohydrate, 240 L of toluene, and 588 L of water were added to a reaction vessel. After purging with nitrogen, stirring was performed at 40 to 50° C. for 1 hour. Subsequently, 62.4 kg of (R)-2-methylglycidyl-4-nitrobenzene sulfonate and 25.4 kg of a 50% aqueous tetra-n-butyl ammonium chloride solution were added. The resulting mixture was refluxed for 3 hours (internal temperature: 87° C.). After the reaction mixture was cooled, 120 L of toluene was added and the resulting mixture was separated into layers. The organic layer was washed with 240 L of water, and concentrated under reduced pressure. After adding 600 L of methanol to the concentrated residue and confirming that the concentrated residue was dissolved, the solution was cooled and stirred at 10° C. or less for 1 hour. After 240 L of water was added, stirring was further performed at 10° C. or less for 30 minutes. The precipitate was filtered. The obtained crystals were washed with 480 L of water to obtain wet crystals.

The wet crystals after washing, 31 kg of 2-chloro-4-nitroimidazole, 17 kg of sodium acetate, and 90 L of t-butyl acetate were placed in a reaction vessel. The resulting mixture was refluxed for 8 hours (internal temperature: 90° C.). After the reaction mixture was cooled, 630 L of methanol was added. Subsequently, cooling was performed at 10° C. or less, and 42 L of a 25% aqueous sodium hydroxide solution was added dropwise at 10° C. or less. Stirring was performed at 10° C. or less for 1 hour and 30 minutes, and stirring was further performed at 10 to 20° C. for 1 hour. After 45 L of ethyl acetate and 45 L of water were added, stirring was performed at 40 to 50° C. for 1 hour. The reaction mixture was cooled to 30° C. or less, and the precipitate was filtered. The obtained precipitate was washed with 270 L of methanol and 360 L of water to obtain wet crystals.

The obtained wet crystals and 900 L of methanol were placed in the reaction vessel. The resulting mixture was refluxed for 1 hour (internal temperature: 65° C.). The reaction mixture was cooled to 30° C. or less, and the precipitate was filtered. The obtained precipitate was washed with 270 L of methanol to obtain crystals. The obtained crystals were dried in air to give 69 kg of crude 1-{4-[(2R)-3-(2-chloro-4-nitroimidazol-1-yl)-2-hydroxy-2-methylpropoxy]phenyl}-4-(4-trifluoromethoxyphenoxy)piperidine (isolation yield: 61%).

69 kg of the crude 1-{4-[(2R)-3-(2-chloro-4-nitroimidazol-1-yl)-2-hydroxy-2-methylpropoxy]phenyl}-4-(4-trifluoromethoxyphenoxy)piperidine was recrystallized in a mixture of 380 L of acetone and 380 L of ethanol. The obtained crystals were dried in air to give 58 kg of 1-{4-[(2R)-3-(2-chloro-4-nitroimidazol-1-yl)-2-hydroxy-2-methylpropoxy]phenyl}-4-(4-trifluoromethoxyphenoxy)piperidine (isolation yield: 84%).

The NMR spectrum data of 1-{4-[(2R)-3-(2-chloro-4-nitroimidazol-1-yl)-2-hydroxy-2-methylpropoxy]phenyl}-4-(4-trifluoromethoxyphenoxy)piperidine are as follows.

$^1$H-NMR (300 MHz, CDCl$_3$) δ ppm: 1.33 (3H, s), 1.88-2.02 (2H, m), 2.03-2.19 (2H, m), 2.95-3.08 (2H, m), 3.30-3.44 (2H, m), 3.81 (1H, d, J=9.4 Hz), 3.85 (1H, d, J=9.4 Hz), 4.15 (1H, d, J=14.3 Hz), 4.28 (1H, d, J=14.3 Hz), 4.37-4.48 (1H, m), 6.81 (2H, d, J=8.6 Hz), 6.87-6.97 (4H, m), 7.14 (2H, d, J=8.6 Hz), 8.01 (1H, s).

Production of (R)-2-methyl-3-(4-(4-(4-(trifluoromethoxy)phenoxy)piperidin-1-yl)phenoxy)propane-1,2-diol p-toluenesulfonate Example 11

3.84 kg of 2-methylallyl alcohol, 0.75 kg of D-(−)-diisopropyl tartrate, and 1.12 kg of molecular sieve (trade name: Zeolum A-3 (produced by Tosoh Corporation)) were dissolved in 28 L of toluene. After purging with nitrogen, the solution was cooled to −20° C. while stirring. After 0.76 kg of titanium isopropoxide was added at −25 to −15° C. and stirring was performed for 30 minutes, 13.2 kg of 80% cumene hydroperoxide was added dropwise at −20 to −10° C. After completion of the dropwise addition, stirring was performed at −20 to −10° C. for 2 hours. After completion of the reaction, 0.52 kg of dimethyl sulfoxide was added at −15 to 15° C., and the temperature was raised to about 15° C. 2.18 kg of dimethyl sulfoxide was added at 15 to 40° C., and stirring was performed at 30 to 50° C. for 3 hours. After the reaction mixture was allowed to stand overnight, 0.56 kg of a diatomaceous filter aid (trade name: silica #600H, produced by Chuo Silika Co., Ltd.) was added. The temperature was raised to 40 to 50° C., and the insoluble matter was removed by hot-filtering. The reaction vessel was washed well with 14 L of toluene. 14 kg of p-toluenesulfonic acid salt of 1-(4-hydroxyphenyl)-4-(4-trifluoromethoxyphenoxy)piperidine, 1.79 kg of lithium hydroxide monohydrate, and 14 L of dimethyl sulfoxide were added to the filtrate. After purging with nitrogen, stirring was performed at 15 to 35° C. for 30 minutes. The temperature was then raised, and stirring was performed under reflux for 2 hours. After stirring, the reaction mixture was cooled to about 70° C. After 70 L of toluene, 2.40 kg of lactic acid, and 28 L of water were added, stirring was performed at 60 to 70° C. for 30 minutes. After the aqueous layer was removed, the organic layer was washed with 24 L of sodium bicarbonate water, and then with 24 L of water. The resulting mixture was concentrated under normal pressure to distill off 42 L of toluene, and the residue was cooled to about 60° C. After 28 L of isopropyl alcohol and 5.32 kg of p-toluenesulfonic acid monohydrate were added, the temperature was adjusted to 50 to 60° C. After crystal precipitation, stirring was performed at 50 to 60° C. for 2 hours. After stirring, the resulting mixture was cooled to 10° C. or less, and the precipitate was filtered. The crystals were washed with a mixed solution of 21 L of toluene and 2.8 L of isopropyl alcohol. The obtained crystals were dried in air. After drying, 12.4 kg of (R)-2-methyl-3-(4-(4-(4-(trifluoromethoxy)phenoxy)piperidin-1-yl)phenoxy)propane-1,2-diol p-toluenesulfonate was obtained (isolation yield: 75.6%).

Production of (R)-1-[4-{(2,3-epoxy-2-methylpropoxy)phenyl}-4-(4-(trifluoromethoxyphenoxy)piperidine)

Example 12

12.0 kg of (R)-2-methyl-3-(4-(4-(4-(trifluoromethoxy)phenoxy)piperidin-1-yl)phenoxy)propane-1,2-diol p-toluenesulfonate, 4.55 kg of triethylamine, and 12 L of cyclopentylmethyl ether were added to the reaction vessel and dissolved by heating at 50° C. or less. After dissolution, the solution was cooled to 0° C. or less, and 2.35 kg of mesyl chloride was added dropwise at 10° C. or less. After completion of the dropwise addition, stirring was performed for 10 minutes. After stirring, 12 L of cyclopentylmethyl ether, 12 L of water, and 12 L of a 25% aqueous sodium hydroxide solution were added, and stirring was performed at 40 to 60° C. for 1 hour and 30 minutes. After stirring, 2.4 L of isopropyl alcohol was added, and stirring was performed. After the aqueous layer was removed, the organic layer was washed with 12 L of water. After washing, a cyclopentylmethyl ether solution was concentrated under reduced pressure. After 60 L of isopropyl alcohol was added to the concentrated residue, the resulting mixture was heated to 60° C. After 24 L of water was added at 50 to 70° C., the resulting mixture was heated and stirred to confirm the dissolution. After confirming the dissolution, the solution was cooled to 30 to 50° C. to confirm crystal precipitation. After confirming the crystal precipitation, stirring was performed at 30 to 50° C. for 1 hour. After stirring, 36 L of water was added. The resulting mixture was cooled to 10° C. or less and stirring was performed at 10° C. or less for 1 hour. After stirring, the precipitate was filtered, and the crystals were washed with 36 L of water. After washing, the obtained crystals were stored as wet crystals (wet yield: 8.39 kg).

The invention claimed is:

1. A method for producing 1-(4-hydroxyphenyl)-4-(4-trifluoromethoxyphenoxy)piperidine represented by Formula (1):

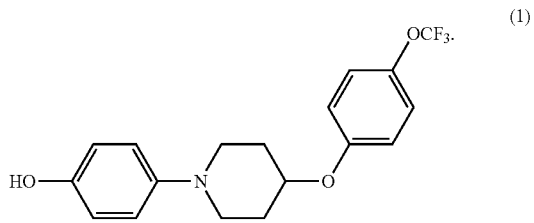

or a salt thereof,
the method comprising the step of heating hydroquinone represented by Formula (2):

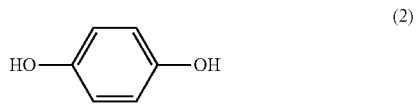

or a salt thereof and
4-(4-trifluoromethoxyphenoxy)piperidine represented by Formula (3):

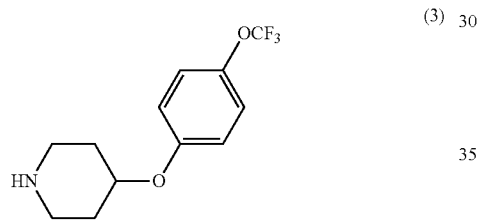

or a salt thereof,
the hydroquinone represented by Formula (2) or a salt thereof being used in an amount of 1.5 moles or more per mole of the 4-(4-trifluoromethoxyphenoxy)piperidine represented by Formula (3) or a salt thereof,
wherein the heating step is performed under an inert atmosphere.

2. The production method according to claim 1, wherein the hydroquinone represented by Formula (2) or a salt thereof is used in an amount of 2 to 10 moles per mole of the 4-(4-trifluoromethoxyphenoxy)piperidine represented by Formula (3) or a salt thereof.

3. The production method according to claim 1, wherein the heating step comprises heating at 150° C. or more.

4. The production method according to claim 1, wherein the heating step is performed under solvent-free conditions.

5. A method for producing the compound represented by Formula (12)

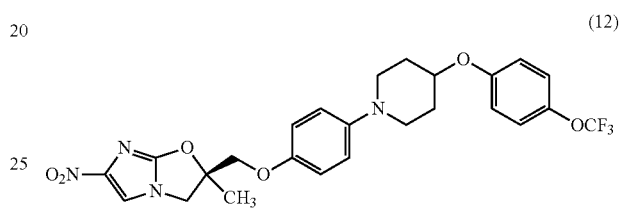

or a salt thereof, the method comprising the steps of:
(a) producing 1-(4-hydroxyphenyl)-4-(4-trifluoromethoxyphenoxy)piperidine or a salt thereof by the method according to claim 1; and
(b) producing the compound represented by Formula (12) or a salt thereof by using the 1-(4-hydroxyphenyl)-4-(4-trifluoromethoxyphenoxy)piperidine or a salt thereof as a starting material,
wherein step (b) comprises mechanism (B1), (B2), or (B3),
mechanism (B1) comprises the steps of:

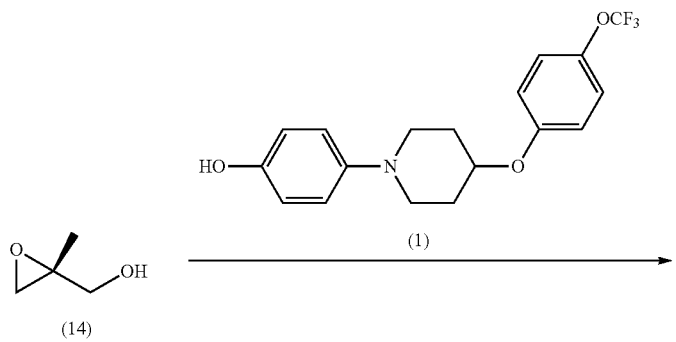

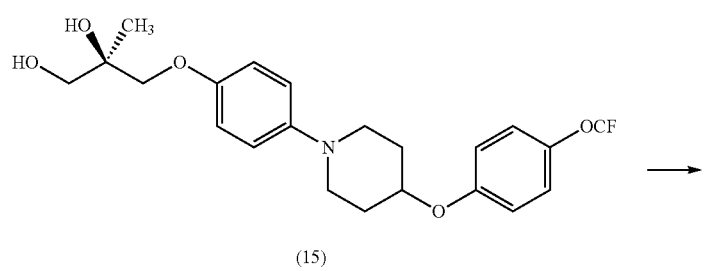

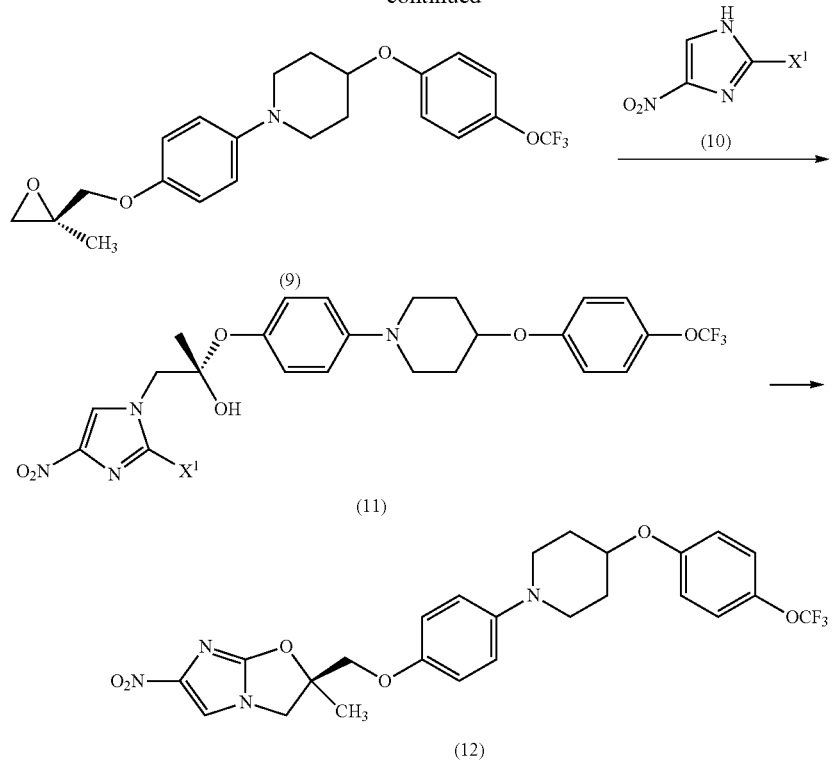

wherein $X^1$ is halogen or nitro, (c2): reacting the compound represented by Formula (14) with the 1-(4-hydroxyphenyl)-4-(4-trifluoromethoxyphenoxy)piperidine or a salt thereof to produce the compound represented by Formula (15) or a salt thereof;

(c3): epoxidating the compound of Formula (15) or a salt thereof to produce the compound represented by Formula (9) or a salt thereof;

(b2): reacting the compound represented by Formula (9) or a salt thereof with a compound represented by Formula (10) to produce a compound represented by Formula (11) or a salt thereof; and (b3): subjecting the compound represented by Formula (11) or a salt thereof to a ring closing reaction to produce the compound represented by Formula (12) or a salt thereof;

mechanism (B2) comprises the steps of:

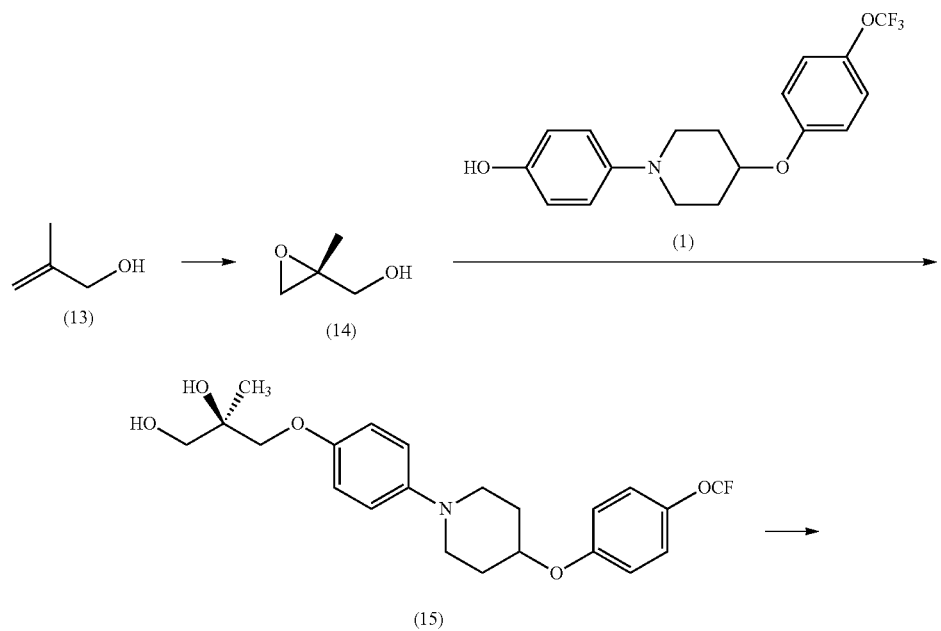

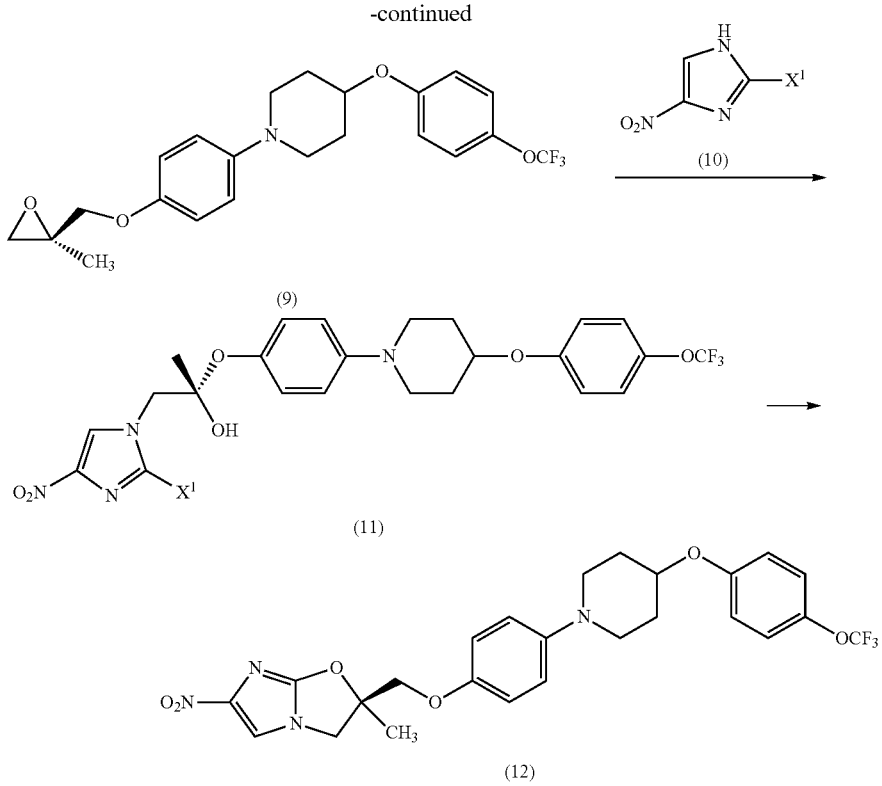

wherein $X^1$ is halogen or nitro, (c1): oxidizing the compound represented by Formula (13) to produce the compound represented by Formula (14);

(c2): reacting the compound represented by Formula (14) with the 1-(4-hydroxyphenyl)-4-(4-trifluoromethoxyphenoxy)piperidine or a salt thereof to produce the compound represented by Formula (15) or a salt thereof;

(c3): epoxidating the compound represented by Formula (15) or a salt thereof to produce the compound represented by Formula (9) or a salt thereof;

(b2): reacting the compound represented by Formula (9) or a salt thereof with the compound represented by Formula (10) to produce the compound represented by Formula (11) or a salt thereof; and (b3): subjecting the compound represented by Formula (11) or a salt thereof to a ring closing reaction to produce the compound represented by Formula (12) or a salt thereof; and mechanism (B3) comprises the steps of:

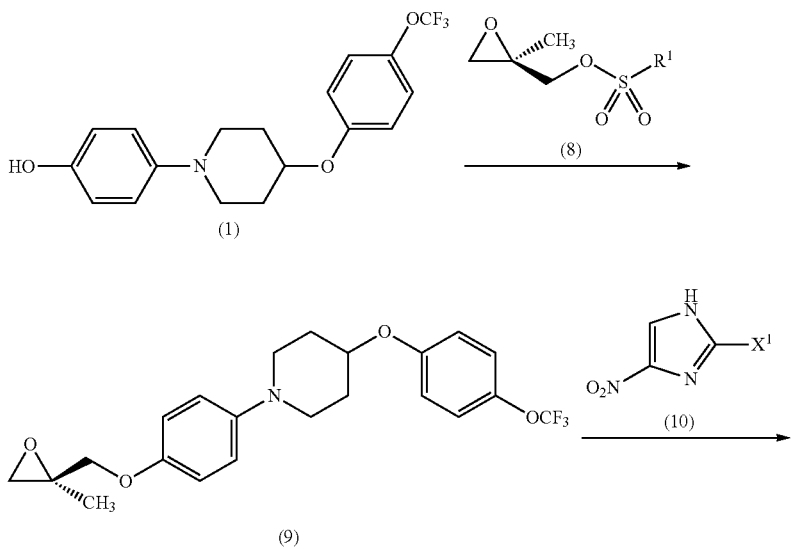

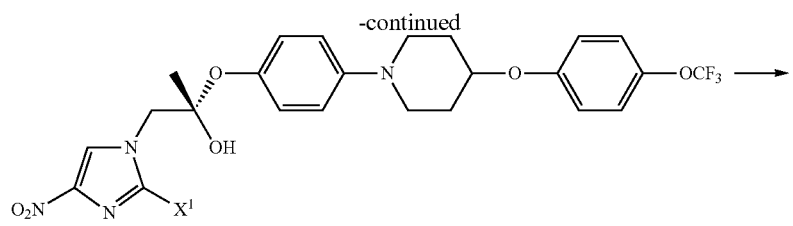

(11)

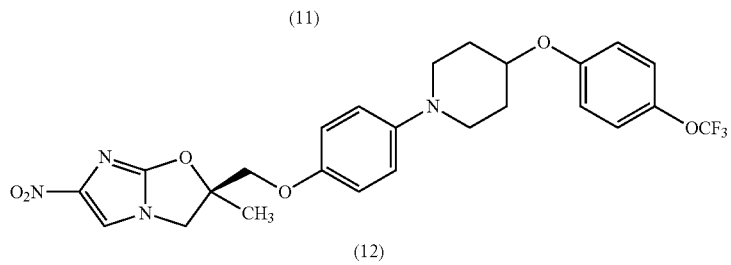

(12)

wherein R¹ is $C_{1-6}$ alkyl optionally having one or more halogens, or phenyl optionally substituted with $C_{1-6}$ alkyl or nitro, and X¹ is halogen or nitro, (b1): reacting the compound of Formula (1) or a salt thereof with a compound represented by Formula (8) or a salt thereof in the presence of a phase transfer catalyst to produce the compound represented by Formula (9) or a salt thereof;

(b2): reacting the compound of Formula (9) or a salt thereof with the compound represented by Formula (10) to produce the compound represented by Formula (11) or a salt thereof; and (b3): subjecting the compound represented by Formula (11) or a salt thereof to a ring closing reaction to produce the compound represented by Formula (12) or a salt thereof.

6. The method according to claim 5, wherein step (b) comprises the mechanism (B1).

7. The method according to claim 5, wherein step (b) comprises the mechanism (B2).

8. The method according to claim 5, wherein step (b) comprises the mechanism (B3).

9. A method for producing the compound represented by Formula (9) or a salt thereof, the method comprising:

producing 1-(4-hydroxyphenyl)-4-(4-trifluoromethoxyphenoxy)piperidine or a salt thereof by the method according to claim 1; and

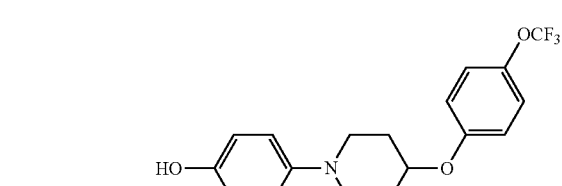

(1)

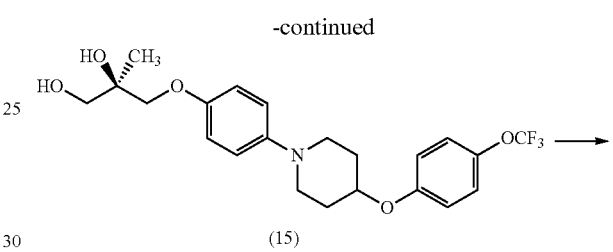

(15)

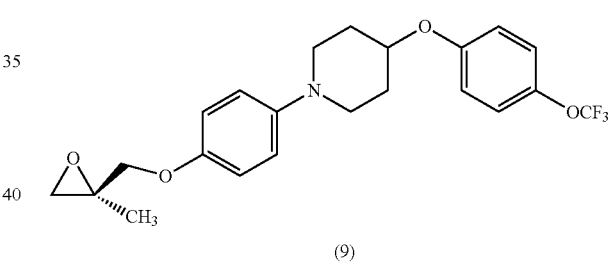

(9)

(c2): reacting the compound represented by Formula (14) with the 1-(4-hydroxyphenyl)-4-(4-trifluoromethoxyphenoxy)piperidine or a salt thereof to produce the compound represented by Formula (15) or a salt thereof; and (c3): epoxidating the compound of Formula (15) or a salt thereof to produce the compound represented by Formula (9) or a salt thereof.

10. A method for producing the compound represented by Formula (9) or a salt thereof, the method comprising:

producing 1-(4-hydroxyphenyl)-4-(4-trifluoromethoxyphenoxy)piperidine or a salt thereof by the method according to claim 1; and

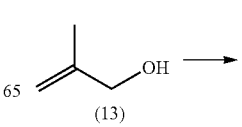

(13)

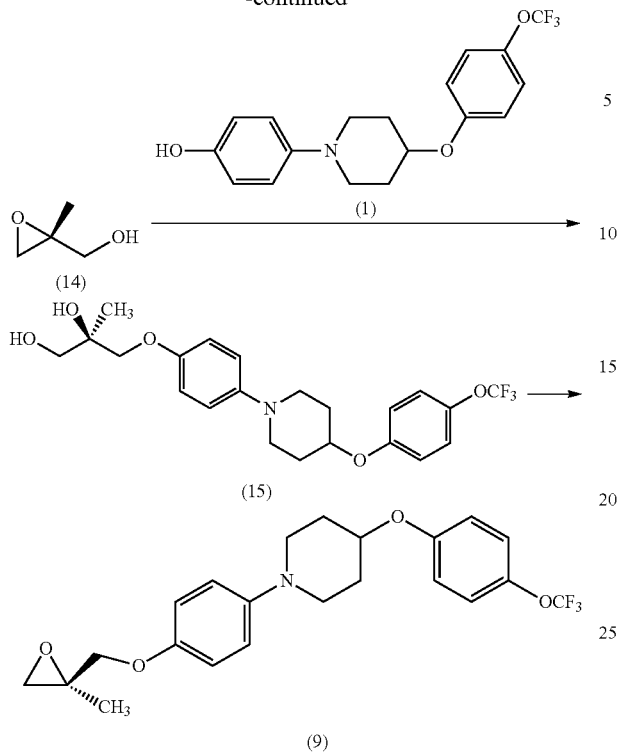

(c1): oxidizing the compound represented by Formula (13) to produce the compound represented by Formula (14);

(c2): reacting the compound represented by Formula (14) with the 1-(4-hydroxyphenyl)-4-(4-trifluoromethoxyphenoxy)piperidine or a salt thereof to produce the compound represented by Formula (15) or a salt thereof; and (c3): epoxidating the compound represented by Formula (15) or a salt thereof to produce the compound represented by Formula (9) or a salt thereof.

11. A method for producing the compound represented by Formula (9) or a salt thereof, the method comprising:

producing 1-(4-hydroxyphenyl)-4-(4-trifluoromethoxyphenoxy)piperidine or a salt thereof by the method according to claim 1; and

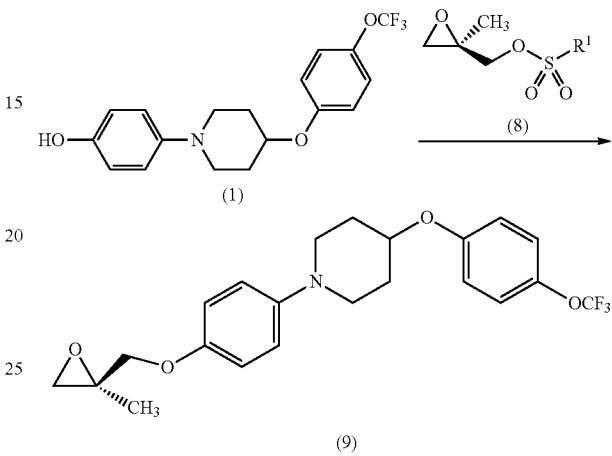

wherein $R^1$ is $C_{1-6}$ alkyl optionally having one or more halogens, or phenyl optionally substituted with $C_{1-6}$ alkyl or nitro, (b1): reacting the 1-(4-hydroxyphenyl)-4-(4-trifluoromethoxyphenoxy)piperidine or a salt thereof with a compound represented by Formula (8) or a salt thereof in the presence of a phase transfer catalyst to produce the compound represented by Formula (9) or a salt thereof.

* * * * *

UNITED STATES PATENT AND TRADEMARK OFFICE
CERTIFICATE OF CORRECTION

PATENT NO.        : 10,252,995 B2
APPLICATION NO.   : 15/561602
DATED             : April 9, 2019
INVENTOR(S)       : Masahiro Miyake, Aya Asahina and Takahiro Okada Page 1 of 1

It is certified that error appears in the above-identified patent and that said Letters Patent is hereby corrected as shown below:

In the Claims

Column 30, Formula 15; In Claim 5, delete " 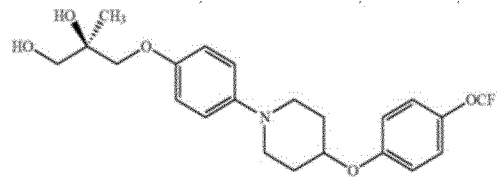 " and insert

-- 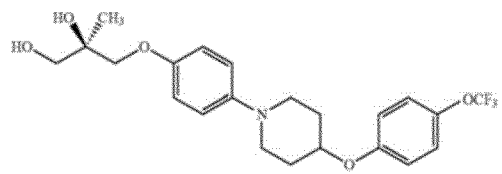 -- therefor

Column 32, Formula 15; In Claim 5, delete " 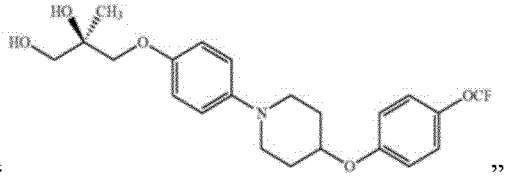 " and insert

-- 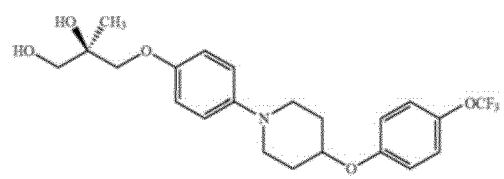 -- therefor

Column 35, Lines 25-26; In Claim 5, delete "the eof" and insert --thereof-- therefor Signed and Sealed this
Thirteenth Day of August, 2019

Andrei Iancu
*Director of the United States Patent and Trademark Office*